United States Patent
Terakado et al.

(10) Patent No.: US 9,771,357 B2
(45) Date of Patent: Sep. 26, 2017

(54) ALXR AGONIST COMPOUND

(71) Applicant: ONO PHARMACEUTICAL CO., LTD., Osaka-shi (JP)

(72) Inventors: Masahiko Terakado, Osaka (JP); Masaya Hirobe, Osaka (JP); Maki Iwahashi, Osaka (JP); Kousuke Tani, Osaka (JP); Tetsuya Sugiyama, Ibaraki (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 14/903,349

(22) PCT Filed: Jul. 8, 2014

(86) PCT No.: PCT/JP2014/068112
§ 371 (c)(1),
(2) Date: Jan. 7, 2016

(87) PCT Pub. No.: WO2015/005305
PCT Pub. Date: Jan. 15, 2015

(65) Prior Publication Data
US 2016/0145249 A1    May 26, 2016

(30) Foreign Application Priority Data

Jul. 9, 2013  (JP) ................................ 2013-143953

(51) Int. Cl.
| | | |
|---|---|---|
| *C07D 417/14* | (2006.01) | |
| *C07D 417/04* | (2006.01) | |
| *A61K 31/454* | (2006.01) | |
| *A61K 31/4545* | (2006.01) | |
| *A61K 45/06* | (2006.01) | |
| *A61K 31/435* | (2006.01) | |

(52) U.S. Cl.
CPC .......... *C07D 417/14* (2013.01); *A61K 31/435* (2013.01); *A61K 31/454* (2013.01); *A61K 31/4545* (2013.01); *A61K 45/06* (2013.01); *C07D 417/04* (2013.01)

(58) Field of Classification Search
CPC .................................................. C07D 417/14
USPC ......................................... 546/194; 514/318
See application file for complete search history.

(56) References Cited

U.S. PATENT DOCUMENTS

| | | |
|---|---|---|
| 2008/0312226 A1 | 12/2008 | Matsumoto et al. |
| 2010/0240619 A1 | 9/2010 | Gregory et al. |
| 2012/0115916 A1 | 5/2012 | Bur et al. |
| 2012/0208842 A1 | 8/2012 | Beard et al. |

FOREIGN PATENT DOCUMENTS

| | | |
|---|---|---|
| JP | 2011-500826 A | 1/2011 |
| JP | 2012-529492 A | 11/2012 |
| WO | 2006/054652 A1 | 5/2006 |
| WO | 2007/115805 A2 | 10/2007 |
| WO | 2009/135581 A2 | 11/2009 |
| WO | 2012/109544 A1 | 8/2012 |

OTHER PUBLICATIONS

Jordan "Tamoxifen . . . " Nature Rev. v.2, p. 205-213 (2003).*
Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Kirk-Othmer Encyclopedia of Chemical Technology, 8, pp. 95-147 (2002).*
Vippagunta et al., "Crystalline Solids", Advanced Drug Delivery Reviews 48 (2001) 3-26.*
Guillory & Morris (in Brittain ed.), "Polymorphism in Pharmaceutical Solids.," NY: Marcel Dekker, Inc., 1999, 1-2, 226. 125-181, 183-226.*
Yu et al., "Physical characterization of, etc.," PSTT, vl. 1(3), 118-127 (1998).*
Braga et al., "Making crystals from . . . " J. Royal Soc. Chem. Commun. p. 3635-3645 (2005).*
Bernstein, "Polymorphism in . . . " p. 115-118, 272 (2002).*
Davidovich et al., "Detection of polymorphism . . . " Am. Pharm. Rev. v.&(1) p. 10, 12, 14, 16, 100 (2004).*
Dean "Analytical Chem . . . " p. 10.24-10.26 (1995).*
Invanisevic et al. "Use of X-ray . . . " Pharm. Sci. Encycl. p. 1-42 (2010).*
Seddon "Pseudopolymorph . . . " Crystal Growth & design v.4(6) p. 1087 (2004) (2 pages from internet).*
Jain et al., "Polymorphism in Pharmacy", Indian Drugs, 1986, 23(6) 315-329.*

(Continued)

*Primary Examiner* — Patricia L Morris
(74) *Attorney, Agent, or Firm* — Sughrue Mion, PLLC

(57) ABSTRACT

The present invention provides a compound having ALXR agonist activity. Specifically, the invention provides a compound having ALXR agonist activity represented by general formula (I) wherein all the symbols are as defined in the specification, a salt thereof, a solvate thereof, or a prodrug thereof as well as an agent containing the same as an active ingredient for preventing and/or treating an ALXR-associated disease, such as an inflammatory bowel disease, an autoimmune disease, a chronic inflammatory disease, asthma, pulmonary fibrosis, atopic dermatitis, ischemia-reperfusion injury, myocardial infarction, or Alzheimer's disease.

(I)

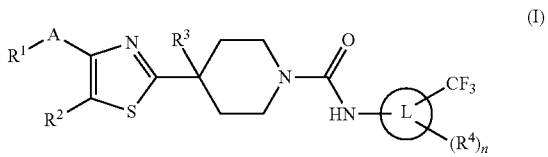

10 Claims, No Drawings

(56) References Cited

OTHER PUBLICATIONS

Wolff, ed., Burger's Medicinal Chemistry and Drug Discovery, 5th edition, NY: John Wiley & Sons, 1996, vol. 1, pp. 949-976.*
Layzer, Degenerative Diseases of the Nervous System, Cecil Textbook of Medicine, 20th Edition, vol. 2, pp. 2050-2057 (1996).*
Damasio, Alzheimer's Disease and Related Dementias, Cecil Textbook of Medicine, 20th Edition, vol. 2, pp. 1992-1996 (1996).*
Robinson "Medical Therapy, etc.," Eur. J. /surg. 1998:Suppl 582:90-98.*
Goh et al., "Lipoxins, etc.," Gastroenterology 2003;124:1043-1054.*
Aslam et al., "What's new, etc.," Curr Opon Allergy Clin Imminol 2014, 14:436-450.*
Dauletbaev et al., "Could relative, etc.," J Allergy Clin Immunol 2016; 137: 1807-8.*
Romano et al., "Lipoxin Receptors" TheScientificWorldJournal (2007), 7, 1393-1412.*
Ramon et al., "Lipoxin A4, etc.," Eur. J. Immunol. 2014, 44: 357-369.*
Chen et al., "Involvement of, etc.," Prostaglandins, Leukotrienes and Essential Fatty Acids 88 (2013) 391-397.*
Zhang, et al.; "Structure-Based Rational Quest for Potential Novel Inhibitors of Human HMG-CoA Reductase by Combining CoMFA 3D QSAR Modeling and Virtual Screening", Journal of Combinatorial Chemistry, vol. 9, No. 1, 2007, 8 pages total.
Database Registry for RN 1023203-45-3, May 28, 2008, RN 1023147-06-9, May 28, 2008, RN 1022392-38-6, May 25, 2008, and RN 1022033-90-4, May 23, 2008, Retrieved from STN International on Aug. 22, 2014, 3 pages total.
Search Report dated Sep. 22, 2014, issued by the International Searching Authority in counterpart International Application No. PCT/JP2014/068112 (PCT/ISA/210).
Written Opinion dated Sep. 22, 2014, issued by the International Searching Authority in counterpart International Application No. PCT/JP2014/068112 (PCT/ISA/237).

* cited by examiner

ALXR AGONIST COMPOUND

BACKGROUND OF THE INVENTION (1) Field of the Invention

The present invention relates to a compound having ALXR agonist activity represented by general formula (I):

[Chemical Formula 1]

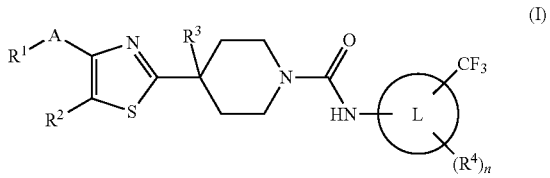

(wherein all the symbols are as defined below), a salt thereof, a solvate thereof, or a prodrug thereof (hereinafter referred to as "compound of the present invention") and also to use thereof.

(2) Description of Related Art

ALXR (also known as: lipoxin A4 receptor, FPRL1 or FPR2) is a G-protein-coupled receptor and forms the family together with FPR1 and FPR3. It has been reported that in ALXR expression cells, the lipoxin A4 (hereinafter abbreviated as LXA4), peptide agonist, or low-molecular-weight agonist induces arachidonic acid production and intracellular $Ca^{2+}$ mobilization via ALXR (Pharmacological Reviews, 2006, Vol. 58, No. 3, pp. 463-487).

LXA4 has been suggested to have anti-inflammatory and inflammation-resolution-promoting effects in various disease model animals. It is said that this inflammation-resolution-promoting effect is attributed to the promotion of the phenomenon that neutrophils that has undergone apoptosis at the location of inflammation is incorporated by macrophages via phagocytosis. It is believed that the conversion of inflammation to the resolution of inflammation is attributed to increased production of prostaglandin and also to enhanced expression of 15-lipoxygenase (hereinafter abbreviated as 15-LO), which is an LXA4 producing enzyme, at the same time. In addition, as another pathway, also in the case where the aspirin-induced acetylation of COX-2 occurs, the enzymatic catalytic activity changes, resulting in the production of epi-LXA4 or epi-LXB4.

It is expected that lipoxins and lipids of epi-lipoxins that interact with ALXR are involved in various inflammatory diseases. In particular, it has been demonstrated that forced expression of 15-LO alleviates the symptom of periodontitis. Meanwhile, the reduction of expression of LXA4 or 15-LO is correlated to the onset of ulcerative colitis or Alzheimer's disease, and LXA4 or its analogue exhibits a suppression effect on pneumonia. In addition, LXA4 or a derivative or stable analog thereof exhibits in vivo effects in disease models of dermatitis, dorsal air pouch, ischemia/reperfusion injury, peritonitis, colitis, mesangioproliferative nephritis, pleuritis, asthma, cystic fibrosis, sepsis, corneal injury, angiogenesis, periodontitis, carrageenan-induced hyperalgesia, graft-vs-host disease (GvHD), etc. (Current Opinion in Pharmacology, 2006, pp. 414-420). Further, ALXR has also been identified as a functional receptor for various peptides including prion protein fragments, human immunodeficiency virus (HIV)-1LAI strain gp120-derived peptides, and amyloid-β1-42 (Ab42) (Protein & Peptide Letters, 2007, Vol. 14, pp. 846-853), and its significant involvement in the cause of Alzheimer's disease has been suggested (FASEB Journal, 2001, Vol. 15, pp. 2454-2462).

Incidentally, the prior art relating to the compound of the present invention includes the following: a fatty acid amide hydrolase inhibitor containing a compound represented by general formula (A):

[Chemical Formula 2]

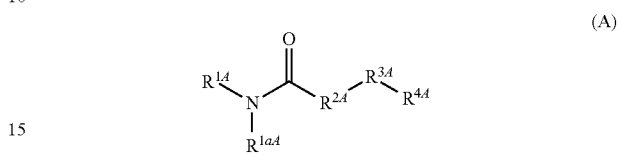

(wherein $R^{1A}$ represents an optionally substituted aryl or an optionally substituted heterocyclic group, $R^{1aA}$ represents a hydrogen atom or the like, $R^{2A}$ represents optionally substituted piperidine-1,4-diyl or the like, $R^{3A}$ represents a thiazole ring or the like, and $R^{4A}$ represents optionally substituted phenyl, an optionally substituted 5- or 6-membered heterocyclic group having one to four heteroatoms selected from an oxygen atom, a sulfur atom, and a nitrogen atom, or the like (partial excerpt from the definition)) (WO 2006/054652, pamphlet); an 11β-hydroxysteroid dehydrogenase inhibitor containing a compound represented by general formula (B):

[Chemical Formula 3]

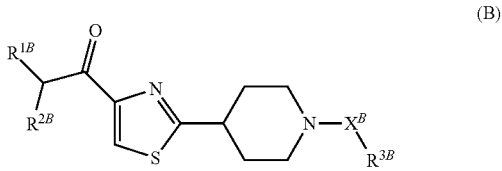

(wherein $R^{1B}$ and $R^{2B}$ represent a 6- to 10-membered saturated monocyclic or bicyclic ring formed together with a nitrogen atom to which they are attached, $X^B$ represents —C(=O)NH— or the like, and $R^{3B}$ represents an optionally substituted aryl, heteroaryl, or the like (partial excerpt from the definition)) (WO 2009/135581, pamphlet); and a hydroxymethylglutaryl-CoA reductase inhibitor represented by the formula:

[Chemical Formula 4]

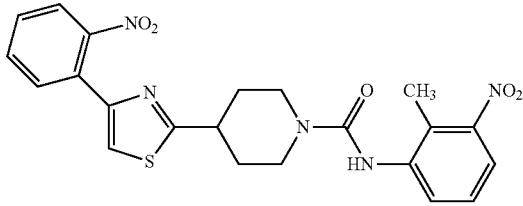

(Journal of Combinatorial Chemistry, 2007, Vol. 9, No. 1, pp. 131-138). However, the compound of the present invention is not described, and it is not suggested that these prior art compounds have ALXR agonist activity either.

SUMMARY OF THE INVENTION

An object of the present invention is to develop a compound having ALXR agonist activity.

The present inventors have conducted extensive research to find a compound having ALXR agonist activity. As a result, they have found a compound represented by general formula (I), etc., and accomplished the present invention.

That is, the present invention is as follows.

[1] A compound represented by general formula (I), a salt thereof, a solvate thereof, or a prodrug thereof:

[Chemical Formula 5]

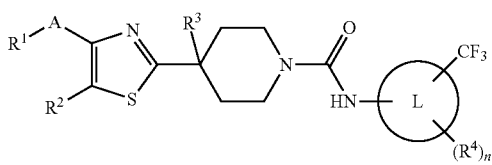

(I)

[wherein

A is a bond, —C(=O)—, —(C($R^5$)$_2$)$_m$—, —CH=CH—, or —C(=O)NH— (wherein $R^5$ represents a hydrogen atom, a hydroxyl group, a methoxy group, or an ethoxy group, and m represents an integer of 1 or 2), ring L represents a phenyl group or a pyridyl group, $R^1$ represents (1) a tert-butyl group or (2) a phenyl group, pyridyl group, or thienyl group optionally substituted with one to three Ys (wherein Y represents a hydroxyl group, a halogen atom, a cyano group, a $C_{1-4}$ alkyl group, a $C_{1-4}$ alkoxy group, or a phenoxy group), $R^2$ represents a hydrogen atom, a $C_{1-3}$ alkyl group, a cyano group, —(C($R^6$)$_2$)$_p$OH (wherein $R^6$ represents a hydrogen atom or a methyl group, and p represents an integer of 1 or 2), or —(CH$_2$)$_q$COR$^7$ (wherein $R^7$ represents a hydroxyl group, a methyl group, an amino group, a methoxy group, or an ethoxy group, and q represents an integer of 0 or 1), $R^3$ represents a hydrogen atom, a hydroxyl group, a halogen atom, a $C_{1-4}$ alkyl group, a cyano group, or —NHR$^8$ (wherein $R^8$ represents a hydrogen atom, an acetyl group, or a methylsulfonyl group), and $R^4$ represents a hydroxyl group, a halogen atom, a $C_{1-4}$ alkyl group, or an amino group, and n represents an integer of 0 to 3, with the proviso that a plurality of Ys, $R^4$s, $R^5$s, and $R^6$s may be the same or different, respectively.]

[2] The compound according [1] above, wherein A is a bond.

[3] The compound according to [1] or [2] above, wherein $R^3$ is a hydrogen atom or a hydroxyl group.

[4] The compound according to any one of [1] to [3] above, wherein $R^2$ is a hydrogen atom, a methyl group, or —CH$_2$OH.

[5] The compound according to any one of [1] to [4] above, wherein $R^1$ is a phenyl group or pyridyl group optionally substituted with one Y.

[6] The compound according to any one of [1] to [5] above, wherein n is 0.

[7] The compound according to claim 1, wherein the compound represented by general formula (I) is represented by general formula (I-1):

[Chemical Formula 6]

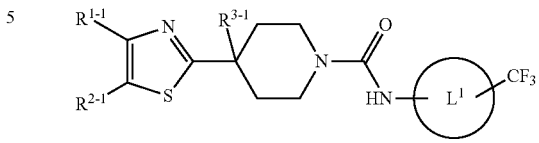

(I-1)

[wherein $R^{1-1}$ represents a phenyl group or pyridyl group optionally substituted with one Y, ring $L^1$ represents a phenyl group or a pyridyl group (wherein the ring $L^1$ is not substituted except for trifluoromethyl group and —NH— group attached thereto), $R^{2-1}$ represents a hydrogen atom or a methyl group, $R^{3-1}$ represents a hydrogen atom or a hydroxyl group, and other symbols are as defined above.]

[8] The compound according to [7] above, wherein in the general formula (I-1), the formula

[Chemical Formula 7]

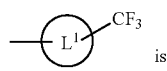

is

[Chemical Formula 8]

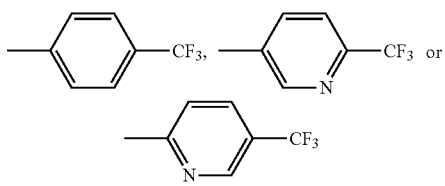

[9] The compound according to [8] above, wherein the compound represented by general formula (I-1) is (1) 4-[4-(3-pyridyl)-1,3-thiazol-2-yl]-N-[4-(trifluoromethyl)phenyl]-1-piperidinecarboxamide, (2) 4-[4-(3-fluorophenyl)-5-methyl-1,3-thiazol-2-yl]-4-hydroxy-N-[4-(trifluoromethyl)phenyl]-1-piperidinecarboxamide, (3) 4-[4-(3-fluorophenyl)-5-methyl-1,3-thiazol-2-yl]-N-[4-(trifluoromethyl)phenyl]-1-piperidinecarboxamide, (4) 4-(4-benzoyl-1,3-thiazol-2-yl)-N-[4-(trifluoromethyl)phenyl]-1-piperidinecarboxamide, or (5) 4-(4-phenyl-1,3-thiazol-2-yl)-N-[5-(trifluoromethyl)-2-pyridyl]-1-piperidinecarboxamide.

[10] A pharmaceutical composition containing a compound represented by general formula (I), a salt thereof, a solvate thereof, or a prodrug thereof as an active ingredient.

[11] An agent for preventing and/or treating an ALXR-associated disease, containing a compound represented by general formula (I), a salt thereof, a solvate thereof, or a prodrug thereof as an active ingredient.

[12] The agent according to [11] above, wherein the ALXR-associated disease is an inflammatory bowel disease, an autoimmune disease, a chronic inflammatory disease, asthma, pulmonary fibrosis, atopic dermatitis, ischemia-reperfusion injury, myocardial infarction, or Alzheimer's disease.

[13] An ALXR agonist containing a compound represented by general formula (I), a salt thereof, a solvate thereof, or a prodrug thereof as an active ingredient.

[14] The agent according to any one of [11] to [13] above, for use in combination with a medicine selected from steroids, anti-TNFα antibodies, anti-IL-6 antibodies, anti-IgE antibodies, nonsteroidal anti-inflammatory drugs, immunosuppressants, sulfasalazine, and mesalazine.

[15] A compound represented by general formula (I), a salt thereof, a solvate thereof, or a prodrug thereof for preventing and/or treating an ALXR-associated disease.

[16] Use of a compound represented by general formula (I), a salt thereof, a solvate thereof, or a prodrug thereof for producing an agent for preventing and/or treating an ALXR-associated disease.

[17] A method for preventing and/or treating an ALXR-associated disease, including administering an effective dose of a compound represented by general formula (I), a salt thereof, a solvate thereof, or a prodrug thereof to a patient in need thereof.

[18] A method for agonizing ALXR activity, including administering an effective dose of a compound represented by general formula (I), a salt thereof, a solvate thereof, or a prodrug thereof to a patient with a disease that can be prevented and/or treated by agonizing ALXR activity.

[19] A product including a compound represented by general formula (I), a salt thereof, a solvate thereof, or a prodrug thereof; a container containing the compound; and a package insert or label that indicates that the compound can be used for preventing and/or treating an ALXR-associated disease.

The compound of the present invention has ALXR agonist activity and thus serves as effective agents for preventing and/or treating a disease that can be prevented or treated by enhancing ALXR activity, such as an inflammatory bowel disease, an autoimmune disease, a chronic inflammatory disease, asthma, pulmonary fibrosis, atopic dermatitis, ischemia-reperfusion injury, myocardial infarction, or the like, or Alzheimer's disease.

DETAILED DESCRIPTION OF PREFERRED EMBODIMENTS

The present invention will be described in detail hereinafter.

Examples of halogen atoms herein include a fluorine atom, a chlorine atom, a bromine atom, and an iodine atom.

Examples of $C_{1-3}$ alkyl groups herein include a methyl group, an ethyl group, a n-propyl group, and an isopropyl group.

Examples of $C_{1-4}$ alkyl groups herein include a methyl group, an ethyl group, a n-propyl group, an isopropyl group, a n-butyl group, an isobutyl group, a sec-butyl group, and a tert-butyl group.

Examples of $C_{1-4}$ alkoxy groups herein include a methoxy group, an ethoxy group, a n-propoxy group, an isopropoxy group, a n-butoxy group, an isobutoxy group, a sec-butoxy group, and a tert-butoxy group.

In the present invention, A is preferably a bond.

In the present invention, $R^3$ is preferably a hydrogen atom or a hydroxyl group.

In the present invention, $R^2$ is preferably a hydrogen atom, a methyl group, or —CH$_2$OH, and more preferably a hydrogen atom or a methyl group.

In the present invention, $R^1$ is preferably a phenyl group optionally substituted with one Y or a pyridyl group optionally substituted with one Y. Y is preferably a halogen atom.

In the present invention, n is preferably 0.

In the present invention, preferred examples of compounds represented by general formula (I) are (1) 4-hydroxy-4-(4-phenyl-1,3-thiazol-2-yl)-N-[4-(trifluoromethyl)phenyl]-1-piperidinecarboxamide,
(2) 4-hydroxy-4-(4-phenyl-1,3-thiazol-2-yl)-N-[5-(trifluoromethyl)-2-pyridyl]-1-piperidinecarboxamide,
(3) 4-hydroxy-4-(4-phenyl-1,3-thiazol-2-yl)-N-[6-(trifluoromethyl)-3-pyridyl]-1-piperidinecarboxamide,
(4) 4-hydroxy-4-(5-methyl-4-phenyl-1,3-thiazol-2-yl)-N-[4-(trifluoromethyl)phenyl]-1-piperidinecarboxamide,
(5) 4-(5-ethyl-4-phenyl-1,3-thiazol-2-yl)-4-hydroxy-N-[4-(trifluoromethyl)phenyl]-1-piperidinecarboxamide,
(6) ethyl 2-(4-hydroxy-1-{[4-(trifluoromethyl)phenyl]carbamoyl}-4-piperidinyl)-4-phenyl-1,3-thiazole-5-carboxylate,
(7) ethyl 4-(2-fluorophenyl)-2-(4-hydroxy-1-{[4-(trifluoromethyl)phenyl]carbamoyl}-4-piperidinyl)-1,3-thiazole-5-carboxylate,
(8) 4-hydroxy-4-[5-(hydroxymethyl)-4-phenyl-1,3-thiazol-2-yl]-N-[4-(trifluoromethyl)phenyl]-1-piperidinecarboxamide,
(9) 4-[4-(2-fluorophenyl)-5-(hydroxymethyl)-1,3-thiazol-2-yl]-4-hydroxy-N-[4-(trifluoromethyl)phenyl]-1-piperidinecarboxamide,
(10) 4-fluoro-4-(5-methyl-4-phenyl-1,3-thiazol-2-yl)-N-[4-(trifluoromethyl)phenyl]-1-piperidinecarboxamide,
(11) 4-hydroxy-4-[4-(6-isopropoxy-3-pyridyl)-1,3-thiazol-2-yl]-N-[4-(trifluoromethyl)phenyl]-1-piperidinecarboxamide,
(12) 4-[4-(4-cyanophenyl)-1,3-thiazol-2-yl]-4-hydroxy-N-[4-(trifluoromethyl)phenyl]-1-piperidinecarboxamide,
(13) 4-hydroxy-4-[4-(3-methylphenyl)-1,3-thiazol-2-yl]-N-[4-(trifluoromethyl)phenyl]-1-piperidinecarboxamide,
(14) 4-hydroxy-4-[4-(2-methoxyphenyl)-1,3-thiazol-2-yl]-N-[4-(trifluoromethyl)phenyl]-1-piperidinecarboxamide,
(15) 4-[4-(4-fluorophenyl)-1,3-thiazol-2-yl]-4-hydroxy-N-[4-(trifluoromethyl)phenyl]-1-piperidinecarboxamide,
(16) 4-[4-(2-fluorophenyl)-5-methyl-1,3-thiazol-2-yl]-4-hydroxy-N-[4-(trifluoromethyl)phenyl]-1-piperidinecarboxamide,
(17) 4-[4-(3-fluorophenyl)-5-methyl-1,3-thiazol-2-yl]-4-hydroxy-N-[4-(trifluoromethyl)phenyl]-1-piperidinecarboxamide,
(18) 4-[4-(4-fluorophenyl)-5-methyl-1,3-thiazol-2-yl]-4-hydroxy-N-[4-(trifluoromethyl)phenyl]-1-piperidinecarboxamide,
(19) 4-[4-(2-cyanophenyl)-5-methyl-1,3-thiazol-2-yl]-4-hydroxy-N-[4-(trifluoromethyl)phenyl]-1-piperidinecarboxamide,
(20) 4-[4-(3-cyanophenyl)-5-methyl-1,3-thiazol-2-yl]-4-hydroxy-N-[4-(trifluoromethyl)phenyl]-1-piperidinecarboxamide,
(21) 4-[4-(4-cyanophenyl)-5-methyl-1,3-thiazol-2-yl]-4-hydroxy-N-[4-(trifluoromethyl)phenyl]-1-piperidinecarboxamide,
(22) 4-hydroxy-4-[4-(2-methoxyphenyl)-5-methyl-1,3-thiazol-2-yl]-N-[4-(trifluoromethyl)phenyl]-1-piperidinecarboxamide,
(23) 4-hydroxy-4-[4-(3-methoxyphenyl)-5-methyl-1,3-thiazol-2-yl]-N-[4-(trifluoromethyl)phenyl]-1-piperidinecarboxamide,
(24) 4-hydroxy-4-[4-(4-methoxyphenyl)-5-methyl-1,3-thiazol-2-yl]-N-[4-(trifluoromethyl)phenyl]-1-piperidinecarboxamide,
(25) 4-hydroxy-4-[5-methyl-4-(3-pyridyl)-1,3-thiazol-2-yl]-N-[4-(trifluoromethyl)phenyl]-1-piperidinecarboxamide,
(26) 4-hydroxy-4-[5-methyl-4-(4-pyridyl)-1,3-thiazol-2-yl]-N-[4-(trifluoromethyl)phenyl]-1-piperidinecarboxamide,

(27) 4-[4-(2-fluorophenyl)-5-methyl-1,3-thiazol-2-yl]-N-[4-(trifluoromethyl)phenyl]-1-piperidinecarboxamide,
(28) 4-[4-(3-fluorophenyl)-5-methyl-1,3-thiazol-2-yl]-N-[4-(trifluoromethyl)phenyl]-1-piperidinecarboxamide,
(29) 4-[4-(4-fluorophenyl)-5-methyl-1,3-thiazol-2-yl]-N-[4-(trifluoromethyl)phenyl]-1-piperidinecarboxamide,
(30) 4-cyano-4-(4-phenyl-1,3-thiazol-2-yl)-N-[4-(trifluoromethyl)phenyl]-1-piperidinecarboxamide,
(31) 4-(5-methyl-4-phenyl-1,3-thiazol-2-yl)-N-[4-(trifluoromethyl)phenyl]-1-piperidinecarboxamide,
(32) 4-(5-methyl-4-phenyl-1,3-thiazol-2-yl)-N-[5-(trifluoromethyl)-2-pyridyl]-1-piperidinecarboxamide,
(33) 4-(4-benzoyl-1,3-thiazol-2-yl)-N-[4-(trifluoromethyl)phenyl]-1-piperidinecarboxamide,
(34) 4-{4-[(E)-2-phenylvinyl]-1,3-thiazol-2-yl}-N-[4-(trifluoromethyl)phenyl]-1-piperidinecarboxamide,
(35) 4-(5-isopropyl-4-phenyl-1,3-thiazol-2-yl)-N-[4-(trifluoromethyl)phenyl]-1-piperidinecarboxamide,
(36) 4-(4-phenyl-1,3-thiazol-2-yl)-N-[4-(trifluoromethyl)phenyl]-1-piperidinecarboxamide,
(37) 4-[4-(4-pyridyl)-1,3-thiazol-2-yl]-N-[4-(trifluoromethyl)phenyl]-1-piperidinecarboxamide,
(38) 4-[4-(2-pyridyl)-1,3-thiazol-2-yl]-N-[4-(trifluoromethyl)phenyl]-1-piperidinecarboxamide,
(39) 4-[4-(3-pyridyl)-1,3-thiazol-2-yl]-N-[4-(trifluoromethyl)phenyl]-1-piperidinecarboxamide,
(40) 4-(4-phenyl-1,3-thiazol-2-yl)-N-[5-(trifluoromethyl)-2-pyridyl]-1-piperidinecarboxamide,
(41) 4-(4-phenyl-1,3-thiazol-2-yl)-N-[6-(trifluoromethyl)-3-pyridyl]-1-piperidinecarboxamide,
(42) 4-{4-[hydroxy(phenyl)methyl]-1,3-thiazol-2-yl}-N-[4-(trifluoromethyl)phenyl]-1-piperidinecarboxamide,
(43) 4-(4-benzyl-1,3-thiazol-2-yl)-N-[4-(trifluoromethyl)phenyl]-1-piperidinecarboxamide,
(44) 4-{4-[ethoxy(phenyl)methyl]-1,3-thiazol-2-yl}-N-[4-(trifluoromethyl)phenyl]-1-piperidinecarboxamide,
(45) 4-[4-(2-phenylethyl)-1,3-thiazol-2-yl]-N-[4-(trifluoromethyl)phenyl]-1-piperidinecarboxamide,
(46) 4-methyl-4-(5-methyl-4-phenyl-1,3-thiazol-2-yl)-N-[4-(trifluoromethyl)phenyl]-1-piperidinecarboxamide,
(47) 4-amino-4-(5-methyl-4-phenyl-1,3-thiazol-2-yl)-N-[4-(trifluoromethyl)phenyl]-1-piperidinecarboxamide,
(48) 4-acetamido-4-(5-methyl-4-phenyl-1,3-thiazol-2-yl)-N-[4-(trifluoromethyl)phenyl]-1-piperidinecarboxamide,
(49) 4-(5-methyl-4-phenyl-1,3-thiazol-2-yl)-4-[(methylsulfonyl)amino]-N-[4-(trifluoromethyl)phenyl]-1-piperidinecarboxamide,
(50) 4-(5-acetyl-4-phenyl-1,3-thiazol-2-yl)-N-[4-(trifluoromethyl)phenyl]-1-piperidinecarboxamide,
(51) 4-[5-(1-hydroxyethyl)-4-phenyl-1,3-thiazol-2-yl]-N-[4-(trifluoromethyl)phenyl]-1-piperidinecarboxamide,
(52) ethyl 4-phenyl-2-(1-{[4-(trifluoromethyl)phenyl]carbamoyl}-4-piperidinyl)-1,3-thiazole-5-carboxylate,
(53) 4-[5-(hydroxymethyl)-4-phenyl-1,3-thiazol-2-yl]-N-[4-(trifluoromethyl)phenyl]-1-piperidinecarboxamide,
(54) 4-phenyl-2-(1-{[4-(trifluoromethyl)phenyl]carbamoyl}-4-piperidinyl)-1,3-thiazole-5-carboxylic acid,
(55) 4-(5-carbamoyl-4-phenyl-1,3-thiazol-2-yl)-N-[4-(trifluoromethyl)phenyl]-1-piperidinecarboxamide,
(56) 4-(5-cyano-4-phenyl-1,3-thiazol-2-yl)-N-[4-(trifluoromethyl)phenyl]-1-piperidinecarboxamide,
(57) 4-[4-(phenylcarbamoyl)-1,3-thiazol-2-yl]-N-[4-(trifluoromethyl)phenyl]-1-piperidinecarboxamide,
(58) 4-{4-[methyl(phenyl)carbamoyl]-1,3-thiazol-2-yl}-N-[4-(trifluoromethyl)phenyl]-1-piperidinecarboxamide,
(59) ethyl 4-(2-thienyl)-2-(1-{[4-(trifluoromethyl)phenyl]carbamoyl}-4-piperidinyl)-1,3-thiazole-5-carboxylate,
(60) ethyl 4-(2-fluorophenyl)-2-(1-{[4-(trifluoromethyl)phenyl]carbamoyl}-4-piperidinyl)-1,3-thiazole-5-carboxylate,
(61) ethyl 4-(3-fluorophenyl)-2-(1-{[4-(trifluoromethyl)phenyl]carbamoyl}-4-piperidinyl)-1,3-thiazole-5-carboxylate,
(62) ethyl 4-(4-fluorophenyl)-2-(1-{[4-(trifluoromethyl)phenyl]carbamoyl}-4-piperidinyl)-1,3-thiazole-5-carboxylate,
(63) ethyl 4-(4-phenoxyphenyl)-2-(1-{[4-(trifluoromethyl)phenyl]carbamoyl}-4-piperidinyl)-1,3-thiazole-5-carboxylate,
(64) ethyl 4-(2-methyl-2-propanil)-2-(1-{[4-(trifluoromethyl)phenyl]carbamoyl}-4-piperidinyl)-1,3-thiazole-5-carboxylate,
(65) methyl [4-phenyl-2-(1-{[4-(trifluoromethyl)phenyl]carbamoyl}-4-piperidinyl)-1,3-thiazol-5-yl]-acetate,
(66) 4-[5-(hydroxymethyl)-4-(2-thienyl)-1,3-thiazol-2-yl]-N-[4-(trifluoromethyl)phenyl]-1-piperidinecarboxamide,
(67) 4-[4-(2-fluorophenyl)-5-(hydroxymethyl)-1,3-thiazol-2-yl]-N-[4-(trifluoromethyl)phenyl]-1-piperidinecarboxamide,
(68) 4-[4-(3-fluorophenyl)-5-(hydroxymethyl)-1,3-thiazol-2-yl]-N-[4-(trifluoromethyl)phenyl]-1-piperidinecarboxamide,
(69) 4-[4-(4-fluorophenyl)-5-(hydroxymethyl)-1,3-thiazol-2-yl]-N-[4-(trifluoromethyl)phenyl]-1-piperidinecarboxamide,
(70) 4-[5-(hydroxymethyl)-4-(4-phenoxyphenyl)-1,3-thiazol-2-yl]-N-[4-(trifluoromethyl)phenyl]-1-piperidinecarboxamide,
(71) 4-[5-(hydroxymethyl)-4-(2-methyl-2-propanil)-1,3-thiazol-2-yl]-N-[4-(trifluoromethyl)phenyl]-1-piperidinecarboxamide, and
(72) 4-[5-(2-hydroxyethyl)-4-phenyl-1,3-thiazol-2-yl]-N-[4-(trifluoromethyl)phenyl]-1-piperidinecarboxamide, as well as salts thereof, solvates thereof, and prodrugs thereof.

In another aspect, examples of the compounds represented by formula (I) are preferably compounds represented by general formula (I-1):

[Chemical Formula 9]

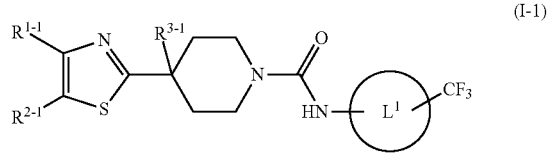

(wherein all the symbols are as defined above), more preferably compounds represented by general formula (I-1), in which the formula

[Chemical Formula 10]

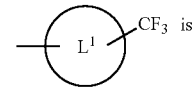

is

[Chemical Formula 11]

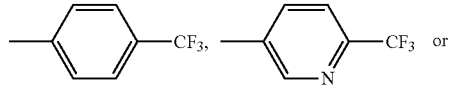

or

-continued

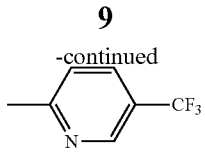

still more preferably
(1) 4-hydroxy-4-(4-phenyl-1,3-thiazol-2-yl)-N-[4-(trifluoromethyl)phenyl]-1-piperidinecarboxamide,
(2) 4-hydroxy-4-(4-phenyl-1,3-thiazol-2-yl)-N-[5-(trifluoromethyl)-2-pyridyl]-1-piperidinecarboxamide,
(3) 4-hydroxy-4-(4-phenyl-1,3-thiazol-2-yl)-N-[6-(trifluoromethyl)-3-pyridyl]-1-piperidinecarboxamide,
(4) 4-hydroxy-4-(5-methyl-4-phenyl-1,3-thiazol-2-yl)-N-[4-(trifluoromethyl)phenyl]-1-piperidinecarboxamide,
(5) 4-hydroxy-4-[4-(6-isopropoxy-3-pyridyl)-1,3-thiazol-2-yl]-N-[4-(trifluoromethyl)phenyl]-1-piperidinecarboxamide,
(6) 4-[4-(4-cyanophenyl)-1,3-thiazol-2-yl]-4-hydroxy-N-[4-(trifluoromethyl)phenyl]-1-piperidinecarboxamide,
(7) 4-hydroxy-4-[4-(3-methylphenyl)-1,3-thiazol-2-yl]-N-[4-(trifluoromethyl)phenyl]-1-piperidinecarboxamide,
(8) 4-hydroxy-4-[4-(2-methoxyphenyl)-1,3-thiazol-2-yl]-N-[4-(trifluoromethyl)phenyl]-1-piperidinecarboxamide,
(9) 4-[4-(4-fluorophenyl)-1,3-thiazol-2-yl]-4-hydroxy-N-[4-(trifluoromethyl)phenyl]-1-piperidinecarboxamide,
(10) 4-[4-(2-fluorophenyl)-5-methyl-1,3-thiazol-2-yl]-4-hydroxy-N-[4-(trifluoromethyl)phenyl]-1-piperidinecarboxamide,
(11) 4-[4-(3-fluorophenyl)-5-methyl-1,3-thiazol-2-yl]-4-hydroxy-N-[4-(trifluoromethyl)phenyl]-1-piperidinecarboxamide,
(12) 4-[4-(4-fluorophenyl)-5-methyl-1,3-thiazol-2-yl]-4-hydroxy-N-[4-(trifluoromethyl)phenyl]-1-piperidinecarboxamide,
(13) 4-[4-(2-cyanophenyl)-5-methyl-1,3-thiazol-2-yl]-4-hydroxy-N-[4-(trifluoromethyl)phenyl]-1-piperidinecarboxamide,
(14) 4-[4-(3-cyanophenyl)-5-methyl-1,3-thiazol-2-yl]-4-hydroxy-N-[4-(trifluoromethyl)phenyl]-1-piperidinecarboxamide,
(15) 4-[4-(4-cyanophenyl)-5-methyl-1,3-thiazol-2-yl]-4-hydroxy-N-[4-(trifluoromethyl)phenyl]-1-piperidinecarboxamide,
(16) 4-hydroxy-4-[4-(2-methoxyphenyl)-5-methyl-1,3-thiazol-2-yl]-N-[4-(trifluoromethyl)phenyl]-1-piperidinecarboxamide,
(17) 4-hydroxy-4-[4-(3-methoxyphenyl)-5-methyl-1,3-thiazol-2-yl]-N-[4-(trifluoromethyl)phenyl]-1-piperidinecarboxamide,
(18) 4-hydroxy-4-[4-(4-methoxyphenyl)-5-methyl-1,3-thiazol-2-yl]-N-[4-(trifluoromethyl)phenyl]-1-piperidinecarboxamide,
(19) 4-hydroxy-4-[5-methyl-4-(3-pyridyl)-1,3-thiazol-2-yl]-N-[4-(trifluoromethyl)phenyl]-1-piperidinecarboxamide,
(20) 4-hydroxy-4-[5-methyl-4-(4-pyridyl)-1,3-thiazol-2-yl]-N-[4-(trifluoromethyl)phenyl]-1-piperidinecarboxamide,
(21) 4-[4-(2-fluorophenyl)-5-methyl-1,3-thiazol-2-yl]-N-[4-(trifluoromethyl)phenyl]-1-piperidinecarboxamide,
(22) 4-[4-(3-fluorophenyl)-5-methyl-1,3-thiazol-2-yl]-N-[4-(trifluoromethyl)phenyl]-1-piperidinecarboxamide,
(23) 4-[4-(4-fluorophenyl)-5-methyl-1,3-thiazol-2-yl]-N-[4-(trifluoromethyl)phenyl]-1-piperidinecarboxamide,
(24) 4-cyano-4-(4-phenyl-1,3-thiazol-2-yl)-N-[4-(trifluoromethyl)phenyl]-1-piperidinecarboxamide,
(25) 4-(5-methyl-4-phenyl-1,3-thiazol-2-yl)-N-[4-(trifluoromethyl)phenyl]-1-piperidinecarboxamide,
(26) 4-(5-methyl-4-phenyl-1,3-thiazol-2-yl)-N-[5-(trifluoromethyl)-2-pyridyl]-1-piperidinecarboxamide,
(27) 4-(4-phenyl-1,3-thiazol-2-yl)-N-[4-(trifluoromethyl)phenyl]-1-piperidinecarboxamide,
(28) 4-[4-(4-pyridyl)-1,3-thiazol-2-yl]-N-[4-(trifluoromethyl)phenyl]-1-piperidinecarboxamide,
(29) 4-[4-(2-pyridyl)-1,3-thiazol-2-yl]-N-[4-(trifluoromethyl)phenyl]-1-piperidinecarboxamide,
(30) 4-[4-(3-pyridyl)-1,3-thiazol-2-yl]-N-[4-(trifluoromethyl)phenyl]-1-piperidinecarboxamide,
(31) 4-(4-phenyl-1,3-thiazol-2-yl)-N-[5-(trifluoromethyl)-2-pyridyl]-1-piperidinecarboxamide, and
(32) 4-(4-phenyl-1,3-thiazol-2-yl)-N-[6-(trifluoromethyl)-3-pyridyl]-1-piperidinecarboxamide, as well as salts thereof, solvates thereof, and prodrugs thereof, and most preferably
(1) 4-[4-(3-pyridyl)-1,3-thiazol-2-yl]-N-[4-(trifluoromethyl)phenyl]-1-piperidinecarboxamide,
(2) 4-[4-(3-fluorophenyl)-5-methyl-1,3-thiazol-2-yl]-4-hydroxy-N-[4-(trifluoromethyl)phenyl]-1-piperidinecarboxamide,
(3) 4-[4-(3-fluorophenyl)-5-methyl-1,3-thiazol-2-yl]-N-[4-(trifluoromethyl)phenyl]-1-piperidinecarboxamide,
(4) 4-(4-benzoyl-1,3-thiazol-2-yl)-N-[4-(trifluoromethyl)phenyl]-1-piperidinecarboxamide, and
(5) 4-(4-phenyl-1,3-thiazol-2-yl)-N-[5-(trifluoromethyl)-2-pyridyl]-1-piperidinecarboxamide, as well as salts thereof, solvates thereof, and prodrugs thereof.

In the present invention, unless otherwise noted, isomers are all encompassed. For example, alkyl groups include linear and branched ones. Further, isomers due to the presence of asymmetric carbon or the like (R-, S-form, α-, β-configuration, enantiomers, diastereomers), optically active substances having optical rotation (D-, L-, d-, l-form), polar compounds obtained by chromatographic separation (high-polarity compounds, low-polarity compounds), equilibrium compounds (e.g., tautomers due to an amide bond, etc.), rotational isomers, and mixtures and racemic mixtures thereof in any proportion are all encompassed by the present invention.

The compound represented by general formula (I) may be converted into a corresponding salt by a known method. The salt is preferably a pharmaceutically acceptable salt. The salt is preferably water-soluble. Examples of suitable salts include acid addition salts (e.g., inorganic acid salts such as hydrochloride, hydrobromide, hydroiodide, sulfate, phosphate, and nitrate, organic acid salts such as acetate, lactate, tartrate, benzoate, citrate, methanesulfonate, ethanesulfonate, benzenesulfonate, toluenesulfonate, isethionate, glucuronate, and gluconate, etc.), salts of alkali metals (potassium, sodium, etc.), salts of alkaline earth metals (calcium, magnesium, etc.), ammonium salts, and salts of pharmaceutically acceptable organic amines (e.g., tetramethylammonium, triethylamine, methylamine, dimethylamine, cyclopentylamine, benzylamine, phenethylamine, piperidine, monoethanolamine, diethanolamine, tris(hydroxymethyl) aminomethane, lysine, arginine, N-methyl-D-glucamine, etc.).

The compound represented by general formula (I) and salt thereof may also be converted into a solvate. The solvate preferable has low toxicity and is preferably water-soluble. Examples of suitable solvates include solvates with water or an alcohol solvent (e.g., ethanol, etc.).

A prodrug of the compound represented by general formula (I) refers to a compound that is converted into the compound represented by general formula (I) by a reaction with an enzyme, gastric acid, or the like in vivo. Specifically, in the case where the compound represented by general formula (I) has an amino group, examples of prodrugs include compounds with the amino group being eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, or tert-butylated; in the case where the compound represented by general formula (I) has a hydroxyl group, examples of prodrugs include compounds with the hydroxyl group being acetylated, palmitoylated, propanoylated, pivaloylated, succinylated, fumarylated, alanylated, or dimethylaminomethylcarbonylated; and in the case where the compound represented by general formula (I) has a carboxy group, examples of prodrugs include compounds with the carboxy group being ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified, or methylamidated. These compounds can be produced by a known method. The prodrug of the compound represented by general formula (I) may be a hydrate or a non-hydrate. The prodrug of the compound represented by general formula (I) may be one that turns into the compound represented by general formula (I) under physiological conditions as described in "*Iyakuhin no Kaihatsu* (Development of Pharmaceuticals)" published by Hirokawa Shoten in 1990, Vol. 7, *"Bunshi Sekkei* (Molecular Design)", pp. 163-198.

Further, atoms forming the compound represented by general formula (I) may each be substituted with its isotope (e.g., $^2H$, $^3H$, $^{13}C$, $^{14}C$, $^{35}S$, $^{125}I$, etc.).

[Method for Producing Compounds of the Present Invention]

The compound of the present invention represented by general formula (I) can be produced, for example, according to the methods shown below, the methods shown in Examples, and the methods equivalent thereto.

Of the compounds represented by general formula (I), a compound represented by general formula (I-1)

[Chemical Formula 12]

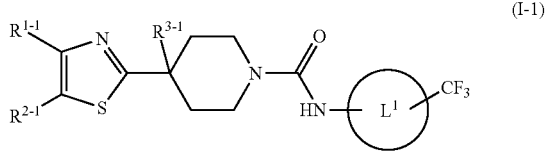

(wherein all the symbols are as defined above), in which ring $L^1$ is a phenyl group, and $R^{3-1}$ is a hydrogen atom, can be produced by a method represented by the following reaction process formula 1:

Reaction process formula 1

[Chemical Formula 13]

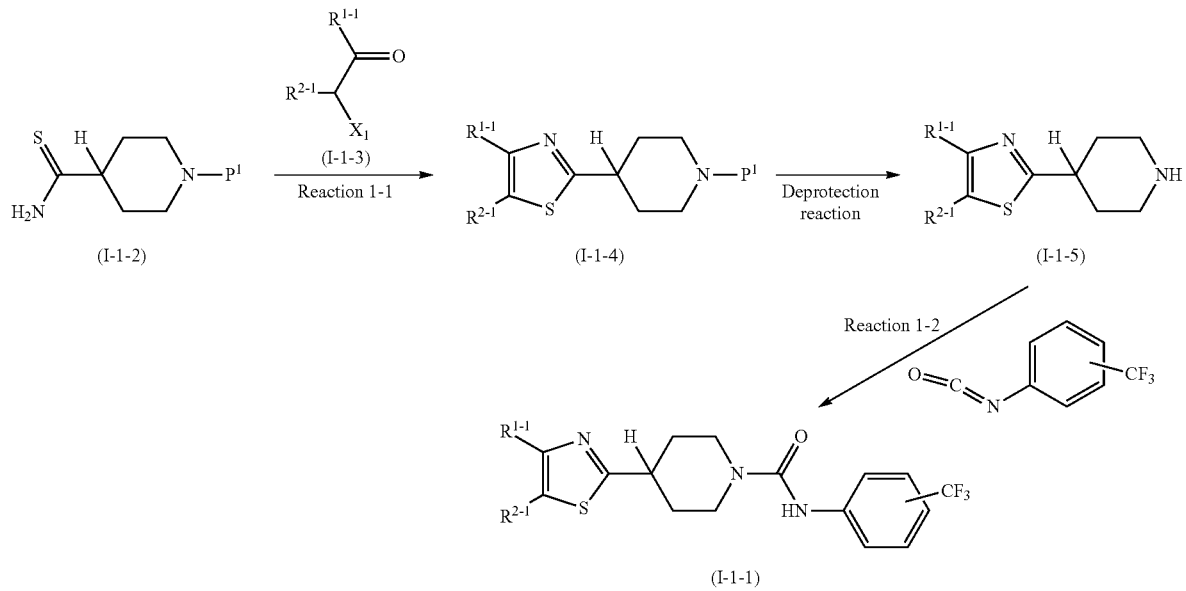

(wherein $P^1$ represents a protective group for the amino group (e.g., a tert-butoxycarbonyl group (boc), a benzyloxycarbonyl group, a fluorenylcarbonyl group, a trityl group, an o-nitrobenzenesulfenyl group, etc.), $X^1$ represents a halogen atom (e.g., a chlorine atom, a bromine atom, etc.), and other symbols are as defined above).

In the reaction process formula 1, reaction 1-1 may be a known reaction. For example, the reaction may be performed by allowing a compound represented by general formula (I-1-2) to react with a compound represented by general formula (I-1-3) at 0° C. to reflux temperature in the presence or absence of a base (e.g., potassium carbonate, sodium carbonate, cesium carbonate, sodium hydride, etc.) in an organic solvent (e.g., tetrahydrofuran, dichloromethane, chloroform, benzene, toluene, xylene, hexane, heptane, cyclohexane, diethyl ether, dioxane, acetone, ethyl methyl ketone, acetonitrile, dimethylsulfoxide, N,N-dimethylformamide, dimethylacetamide, ethyl acetate, etc.) in the presence or absence of a catalyst (e.g., potassium iodide, sodium iodide, tetrabutylammonium iodide, etc.).

In the reaction process formula 1, reaction 1-2 may be a known reaction. For example, the reaction may be performed by allowing a compound represented by general formula (I-1-5) to react with trifluoromethyl phenyl isocyanate at 0° C. to reflux temperature in the presence or absence of a base (e.g., potassium carbonate, sodium carbonate, cesium carbonate, sodium hydride, triethylamine, diisopropylethylamine, N-methylmorpholine, etc.) in an organic solvent (e.g., tetrahydrofuran, dichloromethane, chloroform, benzene, toluene, xylene, hexane, heptane, cyclohexane, diethyl ether, dioxane, acetone, ethyl methyl ketone, acetonitrile, dimethylsulfoxide, N,N-dimethylformamide, dimethylacetamide, ethyl acetate, etc.). It is also possible to use (4-nitrophenyl)N-[4-(trifluoromethyl)phenyl]carbamate in place of trifluoromethyl phenyl isocyanate.

Meanwhile, the compound represented by general formula (I-1), in which ring $L^1$ is a phenyl group, and $R^{3-1}$ is a hydroxyl group, can be produced by a method represented by the following reaction process formula 2:

formed by allowing a compound represented by general formula (I-2-2) to react at 0° C. to reflux temperature in the presence of an acid (e.g., hydrochloric acid, bromic acid, sulfuric acid, phosphoric acid, etc.), in the presence of sodium nitrite, and in the presence of a halogenated metal (e.g., copper (I) chloride, copper (I) bromide, copper (I) iodide, potassium iodide, etc.). In addition, in place of an acid and sodium nitrite, the reaction may also be performed by allowing a compound represented by general formula (I-2-2) to react at 0° C. to reflux temperature under anhydrous conditions in the presence of an alkyl nitrite (e.g., amyl nitrite, tert-butyl nitrite, etc.) and in the presence of a halogenated metal (e.g., copper (I) chloride, copper (I) bromide, copper (I) iodide, etc.) in an organic solvent (e.g., tetrahydrofuran, dichloromethane, chloroform, benzene, toluene, xylene, hexane, heptane, cyclohexane, diethyl ether, dioxane, acetone, ethyl methyl ketone, acetonitrile, dimethylsulfoxide, N,N-dimethylformamide, dimethylacetamide, ethyl acetate, etc.).

Reaction process formula 2

[Chemical Formula 14]

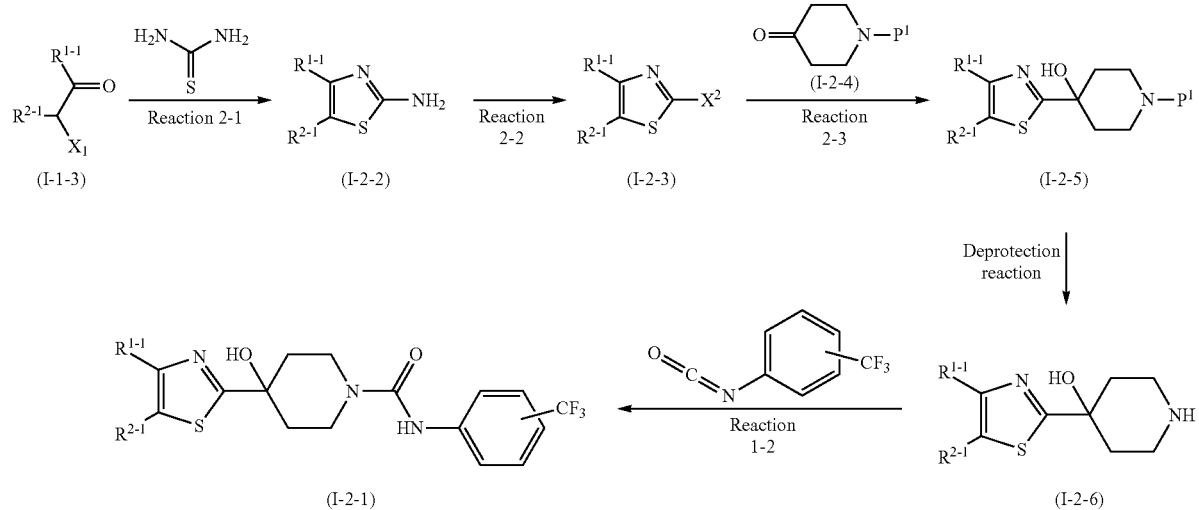

(wherein $X^2$ represents a halogen atom, and other symbols are as defined above).

In the reaction process formula 2, reaction 2-1 may be a known reaction. For example, the reaction may be performed by allowing a compound represented by general formula (I-1-3) to react with thiouric acid at 0° C. to reflux temperature in the presence or absence of a base (e.g., triethylamine, isopropyldiethylamine, potassium carbonate, sodium carbonate, cesium carbonate, sodium hydride, etc.) in an organic solvent (e.g., ethyl alcohol, methyl alcohol, isopropyl alcohol, n-butyl alcohol, dioxane, tetrahydrofuran, dichloromethane, chloroform, benzene, toluene, xylene, hexane, heptane, cyclohexane, diethyl ether, dioxane, acetone, ethyl methyl ketone, acetonitrile, dimethylsulfoxide, N,N-dimethylformamide, dimethylacetamide, ethyl acetate, etc.).

In the reaction process formula 2, reaction 2-2 may be a known reaction. For example, the reaction may be per- In the reaction process formula 2, reaction 2-3 may be a known reaction. For example, the reaction may be performed by stirring a compound represented by general formula (I-2-3) at −78° C. to room temperature in the presence of a base (e.g., a Grignard reagent, lithium diisopropylamine, lithium hexamethyldisilazide, potassium hexamethyldisilazide, sodium hexamethyldisilazide, an alkyllithium (e.g., n-butyllithium), etc.) in an organic solvent (e.g., dioxane, tetrahydrofuran, dichloromethane, toluene, xylene, hexane, heptane, cyclohexane, diethyl ether, dioxane, etc.), and then adding general formula (I-2-4) to the resulting anion to cause a reaction.

The compound represented by general formula (I-1), in which ring $L^1$ is a phenyl group, and $R^{2-1}$ and $R^{3-1}$ are each a hydrogen atom, can be produced by a method represented by the following reaction process formula 3:

Reaction process formula 3

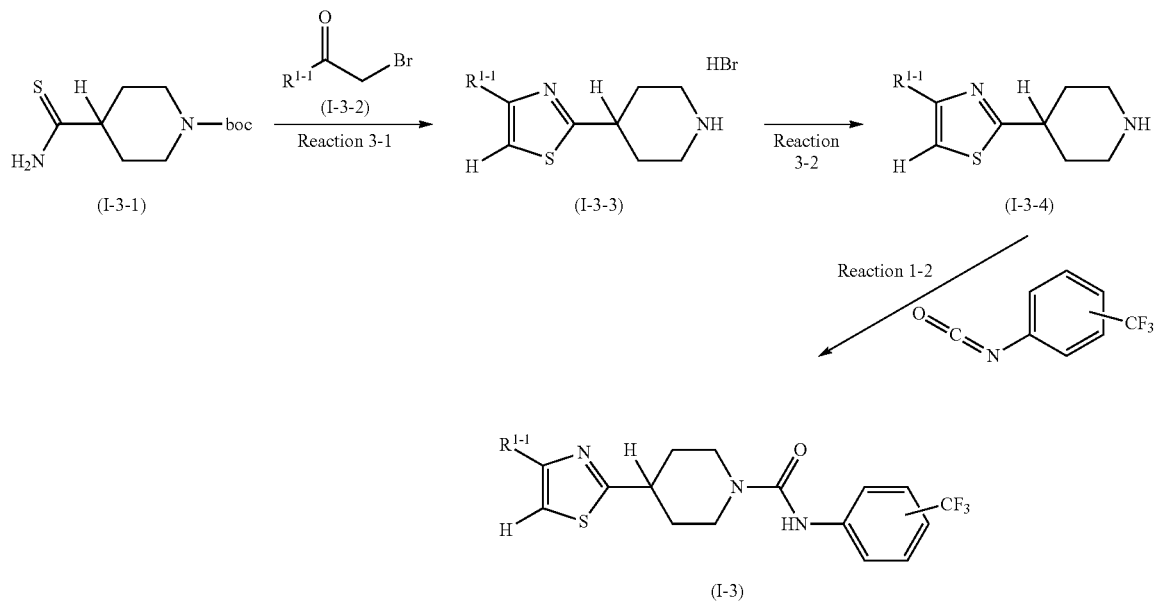

(wherein all the symbols are as defined above).

In the reaction process formula 3, reaction 3-1 may be a known reaction. For example, the reaction may be performed using a flow-type or microchannel reactor provided with a back-pressure control valve. A compound represented by general formula (I-3-1) and a compound represented by general formula (I-3-2) are dissolved each at the same concentration in a solvent (e.g., methanol, ethanol, isopropyl alcohol, tetrahydrofuran, benzene, toluene, xylene, dioxane, acetone, ethyl methyl ketone, acetonitrile, dimethylsulfoxide, N,N-dimethylformamide, dimethylacetamide, etc., or a mixed solvent of such a solvent and water in any proportion), the resulting mixture is fed using a liquid-feeding pump or a syringe pump, and stirred with a T-shaped or static micromixer. Subsequently, in a tube-shaped reaction vessel having an inner diameter of 0.5 to 1.2 mm, the mixture is allowed to react at 0° C. to 150° C. for a predetermined period of reaction time, whereby the reaction can be performed.

In the reaction process formula 3, reaction 3-2 is a known reaction, and can be performed by dissolving a compound represented by general formula (I-3-3) in an organic solvent (e.g., tetrahydrofuran, dichloromethane, chloroform, benzene, toluene, xylene, hexane, heptane, cyclohexane, diethyl ether, dioxane, acetone, ethyl methyl ketone, acetonitrile, dimethylsulfoxide, N,N-dimethylformamide, dimethylacetamide, ethyl acetate, etc.), followed by washing with an aqueous solution of a base (e.g., sodium hydrogen carbonate, potassium carbonate, sodium carbonate, caustic soda, caustic potash, etc.).

The compound represented by general formula (I-1), in which ring $L^1$ is a phenyl group, and $R^{3-1}$ is a hydroxyl group, can also be produced by a method represented by the following reaction process formula 4:

Reaction process formula 4

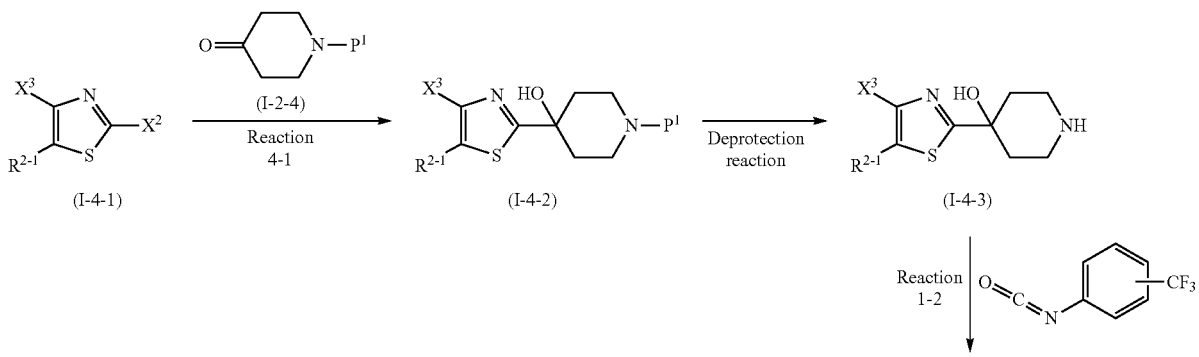

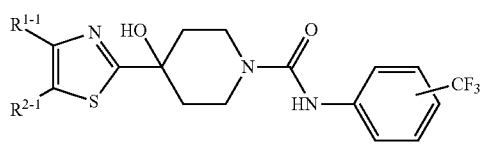 (I-2-1)

-continued

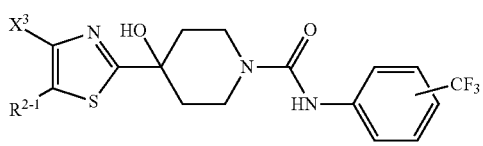 (I-4-4)

$R^{1-1}$—W (I-4-5)
Reaction 4-2

(wherein $X^3$ represents a halogen atom (e.g., a chlorine atom, a bromine atom, etc.), W represents a boronic acid group (—$B(OH)_2$), and other symbols are as defined above).

In the reaction process formula 4, reaction 4-1 can be performed in the same manner as for the reaction 2-3.

In the reaction process formula 4, reaction 4-2 may be a known reaction (Suzuki coupling reaction, etc.). For example, the reaction can be performed by allowing a compound represented by general formula (I-4-4) to react with a compound represented by general formula (I-4-5) at 0° C. to 150° C., for example, for a predetermined period of time in the presence of a base (e.g., an inorganic base such as tripotassium phosphate, potassium carbonate, sodium carbonate, or cesium carbonate, an amine such as triethylamine or diisopropylethylamine, potassium tert-butoxide, sodium tert-butoxide, etc.) and a palladium catalyst (e.g., tetrakis(triphenylphosphine)palladium, palladium acetate, bis(acetonitrile)palladium chloride, etc.) in an organic solvent (e.g., dioxane, tetrahydrofuran, dichloromethane, toluene, xylene, hexane, heptane, cyclohexane, diethyl ether, dioxane, etc.).

In the above reaction process formulae 1, 2, and 4, deprotection reactions for the protective group ($P^1$) for the amino group are well known. Examples thereof include a deprotection reaction through alkali hydrolysis, a deprotection reaction under acidic conditions, a deprotection reaction through hydrogenolysis, a deprotection reaction of a silyl group, a deprotection reaction using a metal, and a deprotection reaction using a metal complex.

For example, the deprotection reaction through alkali hydrolysis is performed, for example, in an organic solvent (methanol, tetrahydrofuran, 1,4-dioxane, or the like alone, or alternatively a mixed solvent of a plurality of these solvents in any proportion) using a hydroxide of an alkali metal (sodium hydroxide, potassium hydroxide, lithium hydroxide, etc.), a hydroxide of an alkaline earth metal (barium hydroxide, calcium hydroxide, etc.), a carbonate (sodium carbonate, potassium carbonate, etc.), an aqueous solution thereof, or a mixture thereof at a temperature of 0 to 40° C.

Meanwhile, the deprotection reaction under acidic conditions is performed, for example, in an organic solvent (dichloromethane, chloroform, 1,4-dioxane, ethyl acetate, anisole, or the like alone, or alternatively a mixed solvent of a plurality of these solvents in any proportion) and in an organic acid (acetic acid, trifluoroacetic acid, methanesulfonic acid, p-toluenesulfonic acid, etc.), an inorganic acid (hydrochloric acid, sulfuric acid, etc.), or a mixture thereof (hydrobromic acid/acetic acid, etc.) at a temperature of 0 to 100° C.

The deprotection reaction through hydrogenolysis is performed, for example, in a solvent (an ether solvent (tetrahydrofuran, 1,4-dioxane, dimethoxyethane, diethyl ether, etc.), an alcohol solvent (methanol, ethanol, etc.), a benzene solvent (benzene, toluene, etc.), a ketone solvent (acetone, methyl ethyl ketone, etc.), a nitrile solvent (acetonitrile, etc.), an amide solvent (N,N-dimethylformamide, etc.), water, ethyl acetate, acetic acid, a mixed solvent of two or more of them, etc.) in the presence of a catalyst (palladium-carbon, palladium black, palladium hydroxide, platinum oxide, Raney-nickel, etc.) in a hydrogen atmosphere at atmospheric pressure or increased pressure or in the presence of ammonium formate at a temperature of 0 to 200° C.

The deprotection reaction of a silyl group is performed, for example, in a water-miscible organic solvent (tetrahydrofuran, acetonitrile, or the like alone, or alternatively a mixed solvent of a plurality of these solvents in any proportion) using tetrabutylammonium fluoride at a temperature of 0 to 40° C.

The deprotection reaction using a metal is performed, for example, in an acidic solvent (acetic acid, a buffer of pH 4.2 to 7.2, or a mixed solution of a solution thereof and an organic solvent such as tetrahydrofuran) in the presence of zinc powder at a temperature of 0 to 40° C. while applying ultrasonic waves or not applying ultrasonic waves.

The deprotection reaction using a metal complex is performed, for example, in an organic solvent (dichloromethane, N,N-dimethylformamide, tetrahydrofuran, ethyl acetate, acetonitrile, 1,4-dioxane, ethanol, etc.), water, or a mixed solvent thereof in the presence of a trap reagent (tributyltin hydride, triethylsilane, dimedone, morpholine, diethylamine, pyrrolidine, etc.), an organic acid (acetic acid, formic acid, 2-ethylhexanoic acid, etc.), and/or an organic acid salt (sodium 2-ethylhexanoate, potassium 2-ethylhexanoate, etc.) and in the presence or absence of a phosphine reagent (triphenylphosphine, etc.) using a metal complex (tetrakis triphenylphosphine palladium (0), bis(triphenylphosphine)palladium (II) dichloride, palladium acetate (II), tris(triphenylphosphine)rhodium (I) chloride, etc.) at a temperature of 0 to 40° C.

In addition to the above examples, the deprotection reaction of the protective group ($P^1$) may also be performed, for example, by the method described in T. W. Greene, Protective Groups in Organic synthesis, Wiley, New York, 1999.

Of the compounds of the present invention represented by general formula (I), a compound other than those shown above can be produced using a combination of known methods, including the method described, for example, in Comprehensive Organic Transformations: A Guide to Functional Group Preparations, 2nd Edition (Richard C. Larock, John Wiley & Sons Inc., 1999), methods obtained by partially modifying known methods, etc.

In each of the reactions herein, the compounds represented by general formula (I-1-2), general formula (I-1-3), general formula (I-2-4), general formula (I-3-1), and general formula (I-3-2) used as raw materials, respectively, are known or can be easily produced by known methods, including Terahedron Letters, 2002, Vol. 43, No. 22, pp. 4059-4061, WO 2000/52032, etc.

In each of the reactions herein, reactions that involve heating can be performed using a water bath, an oil bath, a sand bath, or a microwave, as is apparent to those skilled in the art.

In each of the reactions herein, a solid-phase supported reagent supported on a high polymer (e.g., polystyrene, polyacrylamide, polypropylene, polyethylene glycol, etc.) may be suitably used.

In the each of the reactions herein, the reaction product can be purified by an ordinary purification means such as distillation under atmospheric pressure or reduced pressure, high-speed liquid chromatography using silica gel or magnesium silicate, thin-layer chromatography, or ion-exchange resin, scavenger resin, or column chromatography, or alternatively by washing, recrystallization, or a like method. Purification may be performed for each reaction or may also be performed after the completion of several reactions.

[Toxicity]

The compound of the present invention has low toxicity and thus can be safely used as pharmaceuticals.

[Application to Pharmaceuticals]

The compound of the present invention have ALXR agonist activity and thus are useful for preventing or treating ALXR-associated diseases, examples thereof including inflammatory bowel diseases such as ulcerative colitis and Crohn's disease, autoimmune diseases such as arthritis, rheumatism, systemic lupus erythematosus, and nephritis autoimmune, chronic inflammatory diseases, allergies, atopic dermatitis, HIV-mediated retroviral infection, cardiovascular disorders, nerve inflammation, prion-mediated diseases, neurodegenerative diseases (amyloid-mediated disorders (particularly Alzheimer's disease), frontotemporal lobar degeneration (FTLD), Parkinson's disease, amyotrophic lateral sclerosis (ALS), lysosomal disease, vascular dementia, and other neurodegenerative diseases associated with the aggregation of proteins such as tau, synuclein, and TDP-43), developmental disorders (autism, etc.), psychiatric diseases (schizophrenia, depression, etc.), asthma, pulmonary fibrosis, ischemia-reperfusion injury, and myocardial infarction.

The compound of the present invention may be administered in combination with other medicines for the purpose of (1) complementing and/or enhancing the prevention and/or treatment, (2) improving the kinetics/absorption, reducing the dose, and/or (3) alleviating the side effects.

For example, in the case where the compound of the present invention is used as an agent for preventing and/or treating an inflammatory disease, it may be administered in combination with an anti-inflammatory agent such as steroids, anti-TNFα antibodies, anti-IL-6 antibodies, anti-IgE antibodies, nonsteroidal anti-inflammatory drugs, immunosuppressants, sulfasalazine, and mesalazine.

As steroids, examples of external medicines include clobetasol propionate, diflorasone acetate, fluocinonide, mometasone furoate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclometasone propionate, triamcinolone acetonide, flumetasone pivalate, alclometasone propionate, clobetasone butyrate, prednisolone, beclometasone propionate, and fludroxycortide; examples of internal medicines and injections include cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, and betamethasone; and examples of inhalants include beclometasone propionate, fluticasone propionate, budesonide, flunisolide, triamcinolone, ST-126P, ciclesonide, dexamethasone palomithionate, mometasone furancarbonate, prasterone sulfonate, deflazacort, methylprednisolone suleptanate, and methylprednisolone sodium succinate.

Examples of the anti-TNFα antibodies include infliximab, certolizumab, golimumab, and adalimumab.

Examples of the anti-IL-6 antibodies include tocilizumab.

Examples of the anti-IgE antibodies include omalizumab.

Examples of the nonsteroidal anti-inflammatory drugs include sasapyrine, sodium salicylate, aspirin, aspirin-dialuminate blend, diflunisal, indomethacin, suprofen, ufenamate, dimethylisopropylazulene, bufexamac, felbinac, diclofenac, tolmetin sodium, clinoril, fenbufen, nabumetone, proglumetacin, indomethacin farnesil, acemetacin, proglumetacin maleate, amfenac sodium, mofezolac, etodolac, ibuprofen, ibuprofenpiconol, naproxen, flurbiprofen, flurbiprofen axetil, ketoprofen, fenoprofen calcium, tiaprofen, oxaprozin, pranoprofen, loxoprofen sodium, alminoprofen, zaltoprofen, mefenamic acid, aluminum mefenamate, tolfenamic acid, floctafenine, ketophenylbutazone, oxyphenbutazone, piroxicam, tenoxicam, ampiroxicam, Napageln ointment, epirizole, tiaramide hydrochloride, tinoridine hydrochloride, emorfazone, sulpyrine, migrenin, saridon, Sedes G, Amipylo-N, Sorbon, pyrine cold remedies, acetaminophen, phenacetin, dimetotiazine mesilate, simetride-blending drugs, and non-pyrine cold remedies.

Examples of the immunosuppressants include azathioprine, mercaptopurine, ciclosporin, and tacrolimus.

A combination drug of the compound of the present invention and these other medicine may be administered in the form of a blend drug prepared by blending the two components in one pharmaceutical preparation, or may also be administered in the form of separate pharmaceutical preparations. The administration in the form of separate pharmaceutical preparations includes simultaneous administration and staggered administration. The staggered administration may be such that the compound of the present invention is administered first, and then the other medicine is administered, or may also be such that the other medicine is administered first, and then the compound of the present invention is administered, and the administration methods may be the same as or different from each other.

The dose of the other medicine can be suitably selected based on the clinically used dose. The blending proportions of the compound of the present invention and the other medicine can be suitably selected according to the age and body weight of the administration subject, administration method, administration time, target disease, symptoms, combination, and the like. For example, 0.01 to 100 parts by mass of the other medicine may be used per part by mass the compound of the present invention. Two or more kinds of other medicines may be combined in any proportion and administered. The above other medicines include not only those that have been found to date but also those that will be found in the future.

In order to use the compound of the present invention or a combination drug of the compound of the present invention and the other medicine for the above purpose, it is usually administered systemically or locally and orally or parenterally.

The dose of the compound of the present invention depends on the age, body weight, symptoms, effects of the treatment, administration method, processing time, and the like. Usually, it is orally administered once or several times a day at a dose of 1 µg to 1 g per administration per adult, parenterally administered once or several times a day at a dose of 0.1 µg to 300 mg per administration per adult, or intravenously administered continuously for 1 hour to 24 hours a day.

Needless to say, as described above, the dose varies depending on various conditions, and thus a dose lower than above may be sufficient, while administration at a higher dose may be required.

When the compound of the present invention or a combination drug of the compound of the present invention and the other medicine is administered, it is used in the form of a solid for internal application or a solution for internal application for oral administration, a sustained-release pharmaceutical preparation in oral administration, or an injection, an external medicine, an inhalant, or a suppository for parenteral administration.

Examples of the solids for internal application for oral administration include tablets, pills, capsules, powders, and granules. Capsules include hard capsules and soft capsules.

In such a solid for oral administration, one or more active substances are formed into a pharmaceutical preparation in the usual manner as they are or after being mixed with an excipient (e.g., lactose, mannitol, glucose, microcrystalline cellulose, starch, etc.), a binder (e.g., hydroxypropyl cellulose, polyvinyl pyrrolidone, magnesium aluminometasilicate, etc.), a disintegrant (e.g., calcium fibrinoglycolate, etc.), a lubricant (e.g., magnesium stearate, etc.), a stabilizer, a solubilizer (e.g., glutamic acid, aspartic acid, etc.), or the like. As necessary, the solid may be coated with a coating agent (e.g., white sugar, gelatin, hydroxypropyl cellulose, hydroxypropyl methylcellulose phthalate, etc.), or may also be coated with two or more layers. Further, capsules made of an absorbable material, such as gelatin, are also encompassed.

Examples of the solutions for internal application for oral administration include pharmaceutically acceptable aqueous solutions, suspensions, emulsions, syrups, and elixirs. In such a solution, one or more active substances are dissolved, suspended, or emulsified in a commonly used diluent (e.g., purified water, ethanol, a mixture thereof, etc.). Further, the solution may also contain a wetting agent, a suspending agent, an emulsifier, a sweetener, a flavor, a fragrance, a preservative, a buffer, etc.

The sustained-release pharmaceutical preparations in oral administration are also effective. A gel-forming substance used for such a sustained-release pharmaceutical preparation is a substance that contains a solvent and swells, whereby its colloidal particles are connected to each other to form a three-dimensional network structure, and a jelly-like material having no fluidity can be formed. In a pharmaceutical preparation, the gel-forming substance is mainly used as a binder, a viscosity improver, and a sustained-release base. For example, gum arabic, agar, polyvinyl pyrrolidone, sodium alginate, propylene glycol alginate, carboxyvinyl polymer, carboxymethyl cellulose, sodium carboxymethyl cellulose, guar gum, gelatin, hydroxypropyl methylcellulose, hydroxypropyl cellulose, polyvinyl alcohol, methylcellulose, and hydroxyethyl methylcellulose are usable.

The injections for parenteral administration encompass solutions, suspensions, emulsions, and solid injections that are dissolved or suspended in a solvent before use. The injection is used by dissolving, suspending, or emulsifying one or more active substances in a solvent. Examples of the solvents include distilled water for injection, physiological saline, vegetable oils, alcohols such as propylene glycol, polyethylene glycol, and ethanol, and combinations thereof. Such an injection may further contain a stabilizer, a solubilizer (e.g., glutamic acid, aspartic acid, Polysolvate 80 (registered trademark), etc.), a suspending agent, an emulsifier, a soothing agent, a buffer, a preservative, etc. The injections are sterilized in the final step or produced in an aseptic manner. They may also be used as aseptic solids (e.g., a lyophilized product is produced and, before use, asepticized or dissolved in aseptic distilled water for injection or other solvent).

The external medicine for parenteral administration may be in the form of, for example, nebulas, inhalants, sprays, aerosols, ointments, gels, creams, poultices, patches, liniments, nasal drops, or the like. Such a medicine contains one or more active substances and is prepared according to a known method or a commonly used formulation.

Nebulas, inhalants, and sprays may contain, in addition to a commonly used diluent, a stabilizer such as sodium hydrogen sulfite and a buffer that provides isotonicity, for example, an isotonic agent such as sodium chloride, sodium citrate, or citric acid. A method for producing a spray is described, for example, in U.S. Pat. Nos. 2,868,691 and 3,095,355 in detail.

Examples of the inhalants for parenteral administration include aerosols, powders for inhalation, and solutions for inhalation. The solution for inhalation may be in such a form that it is dissolved or suspended in water or other proper medium before use.

These inhalants are produced according to a known method.

For example, for the preparation of the solution for inhalation, antiseptics (e.g., benzalconium chloride, paraben, etc.), colorants, buffering agents (e.g., sodium phosphate, sodium acetate, etc.), isotonic agents (e.g., sodium chloride, concentrated glycerin, etc.), thickeners (e.g., carboxyvinyl polymer, etc.), absorption enhancers, and the like are suitably selected as necessary.

For the preparation of the powder for inhalation, lubricants (e.g., stearic acid, a salt thereof, etc.), binders (e.g., starch, dextrin, etc.), excipients (e.g., lactose, cellulose, etc.), colorants, antiseptics (e.g., benzalconium chloride, paraben, etc.), absorption enhancers, and the like are suitably selected as necessary.

For the administration of the solution for inhalation, a sprayer (e.g., atomizer, nebulizer, etc.) is usually used, while for the administration of the powder for inhalation, a powder medicine inhaler is usually used.

The ointments are produced according to a known or commonly used formulation. For example, the ointment is prepared by mingling one or more active substances with or melting one or more active substances in a base. The ointment base is selected from known or commonly used ones. For example, the ointment base is selected from higher fatty acids and higher fatty acid esters (e.g., adipic acid, myristic acid, palmitic acid, stearic acid, oleic acid, adipate, myristate, palmitate, stearate, oleate, etc.), waxes (e.g., beeswax, spermaceti wax, ceresin, etc.), surfactants (e.g., polyoxyethylene alkyl ether phosphate, etc.), higher alcohols (e.g., cetanol, stearyl alcohol, cetostearyl alcohol, etc.), silicone oils (e.g., dimethylpolysiloxane, etc.), hydrocarbons (e.g., hydrophilic petrolatum, white petrolatum, purified lanolin, liquid paraffin, etc.), glycols (e.g., ethylene glycol, diethylene glycol, propylene glycol, polyethylene glycol, macrogol, etc.), vegetable oils (e.g., castor oil, olive oil, sesame oil, turpentine oil, etc.), animal oils (e.g., mink oil, egg yolk oil, squalane, squalene, etc.), water, absorption enhancers, and rash inhibitors. The ointment bases are used alone or as a mixture of two or more kinds. Further, the ointments may contain moisturizers, preservatives, stabilizers, antioxidants, flavors, and the like.

The gels are produced according to a known or commonly used formulation. For example, the gel is prepared by melting one or more active substances in a base. The gel base is selected from known or commonly used ones. For example, the gel base is selected from lower alcohols (e.g., ethanol, isopropyl alcohol, etc.), gelatinizers (e.g., carboxymethyl cellulose, hydroxyethyl cellulose, hydroxypropyl cellulose, ethyl cellulose, etc.), neutralizers (e.g., triethanolamine, diisopropanolamine, etc.), surfactants (e.g., polyethylene glycol monostearate, etc.), gums, water, absorption enhancers, and rash inhibitors. The gel bases are used alone or as a mixture of two or more kinds. Further, the gels may contain preservatives, antioxidants, flavors, and the like.

The creams are produced according to a known or commonly used formulation. For example, the cream is produced by melting or emulsifying one or more active substances in a base. The cream base is selected from known or commonly used ones. For example, the cream base is selected from higher fatty acid esters, lower alcohols, hydrocarbons, polyhydric alcohols (e.g., propylene glycol, 1,3-butylene glycol, etc.), higher alcohols (e.g., 2-hexyldecanol, cetanol, etc.), emulsifiers (e.g., polyoxyethylene alkyl ethers, fatty acid esters, etc.), water, absorption enhancers, and rash inhibitors. The cream bases are used alone or as a mixture of two or more kinds. Further, the creams may contain preservatives, antioxidants, flavors, and the like.

The poultices are produced according to a known or commonly used formulation. For example, the poultice is produced by melting one or more active substances in a base, kneading, followed by uniformly coating on a support. The poultice base is selected from known or commonly used ones. For example, the poultice base is selected from thickeners (e.g., polyacrylic acid, polyvinyl pyrrolidone, gum arabic, starch, gelatin, methylcellulose, etc.), wetting agents (e.g., urea, glycerin, propylene glycol, etc.), fillers (e.g., kaolin, zinc oxide, talc, calcium, magnesium, etc.), water, solubilizers, tackifiers, and rash inhibitors. The poultice bases are used alone or as a mixture of two or more kinds. Further, the poultices may contain preservatives, antioxidants, flavors, and the like.

The patches are produced by a known or commonly used formulation. For example, the patch is produced by melting one or more active substances in a base, and uniformly coating the melt on a support. The patch base is selected from known or commonly used ones. For example, the patch base is selected from polymer bases, fats and oils, higher fatty acids, tackifiers, and rash inhibitors. The patch bases are used alone or as a mixture of two or more kinds. Further, the patches may contain preservatives, antioxidants, flavors, and the like.

The liniments are produced according to a known or commonly used formulation. For example, the liniment is prepared by dissolving, suspending, or emulsifying one or more active substances in at least one kind selected from water, alcohols (e.g., ethanol, polyethylene glycol, etc.), higher fatty acids, glycerin, soaps, emulsifiers, suspending agents, and the like. Further, the liniments may contain preservatives, antioxidants, flavors, and the like.

Examples of other compositions for parenteral administration include suppositories for intrarectal administration and pessaries for intravaginal administration containing one or more active substances and formulated in the usual manner.

The contents of all the patent literatures, non-patent literatures, and references explicitly referred to herein are incorporated herein by reference in their entirety.

EXAMPLES

Hereinafter, the present invention will be described in detail with reference to Examples and Biological Examples, but the present invention is not limited thereby. The compound of the present invention and compounds shown in the Examples were named according to the ACD/Name (Version 6.00, Advanced Chemistry Development Inc.). According to this nomenclature, for example, a compound having the following structure:

[Chemical Formula 17]

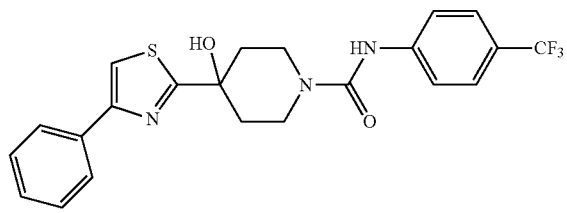

is named as 4-hydroxy-4-(4-phenyl-1,3-thiazol-2-yl)-N-[4-(trifluoromethyl)phenyl]-1-piperidinecarboxamide.

The solvents shown in parenthesis in the section of separation by chromatography and in TLC represent eluting solvents or developing solvents used, and the ratios are by volume. Numerical values shown in the section of NMR are the $^1$H-NMR values measured using the specified measurement solvents.

Example 1

2-Methyl-2-propanil 4-hydroxy-4-(4-phenyl-1,3-thiazol-2-yl)-1-piperidinecarboxylate

[Chemical Formula 18]

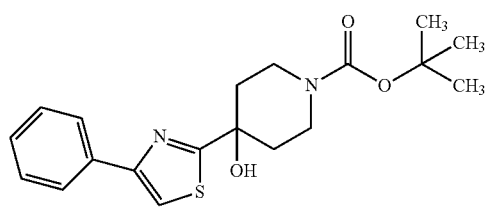

2-Bromo-4-phenylthiazole (1.0 g) was dissolved in tetrahydrofuran (5 mL), and an isopropylmagnesium chloride lithium chloride tetrahydrofuran solution (15%, 3.4 mL) was added at −15° C. and stirred for 15 minutes. Subsequently, 1-(tert-butoxycarbonyl)-4-piperidone (0.83 g) was added thereto and further stirred at −15° C. for 30 minutes. Water (20 mL) was added to the reaction solution, followed by extraction twice with ethyl acetate (30 mL). The organic layer was washed with saturated saline (20 mL), then dried using anhydrous sodium sulfate, and concentrated under reduced pressure. The resulting light brown solid was washed with tert-butyl methyl ether and then dried under reduced pressure to give the title compound (1.31 g) having the following physical properties.

TLC: Rf 0.70 (hexane:ethyl acetate=1:1);

$^1$H-NMR (CDCl$_3$): δ7.91-7.83 (m, 2H), 7.45-7.28 (m, 3H), 4.14-3.90 (m, 2H), 3.40-3.20 (m, 2H), 3.13 (s, 1H), 2.15 (dt, J=4.2, 13.2 Hz, 2H), 1.95-1.83 (m, 2H), 1.48 (s, 9H).

Example 2

4-(4-Phenyl-1,3-thiazol-2-yl)-4-piperidinol hydrochloride

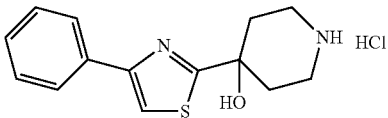

[Chemical Formula 19]

The compound produced in Example 1 (1.17 g) was dissolved in 1,4-dioxane (4 mL), then a 4 N hydrogen chloride/1,4-dioxan solution (3.25 mL) was added and stirred at room temperature for 3 hours, and the resulting crystals were collected by filtration. The crystals were dried under reduced pressure to give the title compound (850 mg) having the following physical properties.

TLC: Rf 0.68 (chloroform:methanol:water=50:10:1);

$^1$H-NMR (DMSO-d$_6$): δ 9.22 (bs, 1H), 8.90 (bs, 1H), 8.03 (s, 1H), 7.91 (d, J=7.2 Hz, 2H), 7.43 (t, J=7.2 Hz, 2H), 7.37-7.27 (m, 2H), 3.35-3.04 (m, 5H), 2.43-2.26 (m, 2H), 2.04-1.89 (m, 2H).

Example 3

4-Hydroxy-4-(4-phenyl-1,3-thiazol-2-yl)-N-[4-(trifluoromethyl)phenyl]-1-piperidinecarboxamide The compound produced in Example 2 (600 mg) was dissolved in methylene chloride (15 mL), and triethylamine (0.28 mL) and 4-(trifluoromethyl)phenyl isocyanate (0.3 mL) were added and stirred for 1 hour under ice-cooling. An aqueous saturated sodium hydrogen carbonate solution (30 mL) was added to the reaction solution, followed by extraction twice with methylene chloride (20 mL). The organic layer was washed with saturated saline, then dried over anhydrous sodium sulfate, and concentrated under reduced pressure. The resulting residue was purified by silica gel column chromatography (methylene chloride:hexane=9:1) to give the title compound (800 mg) having the following physical properties.

TLC: Rf 0.44 (chloroform:methanol=10:1);

$^1$H-NMR (DMSO-d$_6$): δ 8.94 (s, 1H), 7.98 (s, 1H), 7.91 (d, J=7.5 Hz, 2H), 7.70 (d, J=9 Hz, 2H), 7.57 (d, J=9 Hz, 2H), 7.40 (t, J=7.5 Hz, 2H), 7.31 (d, J=7.5 Hz, 1H), 6.25 (s, 1H), 4.12-3.98 (m, 2H), 3.30-3.20 (m, 2H), 2.18-2.03 (m, 2H), 1.88-1.73 (m, 2H).

Example 4

4-Hydroxy-4-(4-phenyl-1,3-thiazol-2-yl)-N-[5-(trifluoromethyl)-2-pyridyl]-1-piperidinecarboxamide 5-Trifluoromethylpyridin-2-amine (1.16 g) was dissolved in methylene chloride (5 mL), then pyridine (0.77 mL) and 2,2,2-trichloroethyl chloroformate (1.69 g) were added and stirred for 30 minutes, and the resulting crystals were collected by filtration. The crystals were dried under reduced pressure to give 2,2,2-trichloroethyl N-[5-(trifluoromethyl)-2-pyridyl]carbamate (1.54 g).

The compound produced in Example 2 (105 mg) was dissolved in dimethylsulfoxide (1 mL), and diisopropylethylamine (114 mg) and 2,2,2-trichloroethyl N-[5-(trifluoromethyl)-2-pyridyl]carbamate (100 mg) were added and stirred at 70° C. for two days. Water (30 mL) was added to the reaction solution, followed by extraction twice with ethyl acetate (20 mL). The organic layer was washed with saturated saline (20 mL), then dried using anhydrous sodium sulfate, and concentrated under reduced pressure. The resulting residue was purified by silica gel column chromatography (hexane:ethyl acetate=8:2) to give the title compound (29 mg) having the following physical properties.

TLC: Rf 0.60 (hexane:ethyl acetate=1:1);

$^1$H-NMR (CDCl$_3$): δ 8.45 (s, 1H), 8.19 (d, J=8.7 Hz, 1H), 7.93-7.81 (m, 3H), 7.56-7.29 (m, 5H), 4.15-4.00 (m, 2H), 3.63-3.45 (m, 2H), 3.28 (brs, 1H), 2.26 (dt, J=13.8, 3.6 Hz, 2H), 2.08-1.95 (m, 2H).

Example 5

4-Hydroxy-4-(4-phenyl-1,3-thiazol-2-yl)-N-[6-(trifluoromethyl)-3-pyridyl]-1-piperidinecarboxamide Triphosgene (62 mg) was dissolved in tetrahydrofuran (2 mL), and triethylamine (64 mg) was added under ice-cooling. After the mixture was stirred for 1 hour under ice-cooling, the compound produced in Example 2 (150 mg) was added thereto and the resulting mixture was stirred at room temperature for 3 hours. Water (2 mL) was added to the reaction solution, followed by extraction twice with ethyl acetate (2 mL). The organic layer was washed with saturated saline (2 mL), then dried using anhydrous sodium sulfate, and concentrated under reduced pressure. The resulting residue was purified by silica gel column chromatography (hexane:ethyl acetate=7:3) to give the title compound (54 mg) having the following physical properties.

TLC: Rf 0.69 (acetate);

$^1$H-NMR (CDCl$_3$): δ 8.51 (d, J=3.0 Hz, 1H), 8.27 (dd, J=8.4, 3.0 Hz, 1H), 7.89 (d, J=8.7 Hz, 2H), 7.64 (d, J=8.4 Hz, 1H), 7.48 (s, 1H), 7.43 (t, J=8.7 Hz, 2H), 7.39-7.30 (m, 1H), 6.68 (s, 1H), 4.12-4.00 (m, 2H), 3.65-3.49 (m, 2H), 3.24 (s, 1H), 2.28 (dt, J=12.9, 4.5 Hz, 2H), 2.10-2.00 (m, 2H).

Example 6

5-Methyl-4-phenyl-1,3-thiazol-2-amine

[Chemical Formula 20]

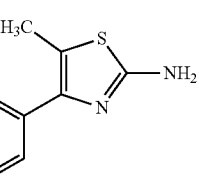

2-Bromo-1-phenylpropan-1-one (5 g), thiourea (1.78 g), and ethyl alcohol (150 mL) were heated under reflux for 3 hours. The reaction solution was cooled, and the solvent was distilled off under reduced pressure. The resulting residue was dissolved in methylene chloride (400 mL), washed with an aqueous saturated sodium carbonate solution, and dried over sodium sulfate. The desiccant was removed by filtration, followed by concentration under reduced pressure, thereby giving the title compound (4.3 g) having the following physical properties.

TLC: Rf 0.10 (hexane:acetate=9:1);

$^1$H-NMR (CDCl$_3$): δ 7.6-7.5 (m, 2H), 7.4-7.3 (m, 2H), 7.3-7.2 (m, 1H), 4.80 (brs, 2H), 2.40 (s, 3H).

Example 7

2-Bromo-5-methyl-4-phenyl-1,3-thiazole

[Chemical formula 21]

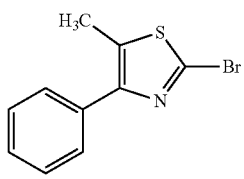

A solution of the compound produced in Example 6 (2.0 g) and copper (II) bromide (3.5 g) in acetonitrile (100 mL) was cooled to 0° C., and pentyl nitrite (1.8 g) was slowly added and stirred at room temperature for 20 hours. An aqueous saturated sodium carbonate solution was added to the reaction solution, followed by extraction with methylene chloride, and then the organic layer was washed with saturated saline and dried over anhydrous sodium sulfate. The solvent was distilled off under reduced pressure, and the resulting residue was purified by silica gel column chromatography (hexane:methylene chloride=9:1) to give the title compound (1.6 g) having the following physical properties.

TLC: Rf 0.70 (hexane:acetate=9:1);

$^1$H-NMR (CDCl$_3$): δ 7.62-7.58 (m, 2H), 7.45-7.25 (m, 3H), 2.55 (s, 3H).

Example 8

2-Methyl-2-propanil 4-hydroxy-4-(5-methyl-4-phenyl-1,3-thiazol-2-yl)-1-piperidinecarboxylate

[Chemical Formula 22]

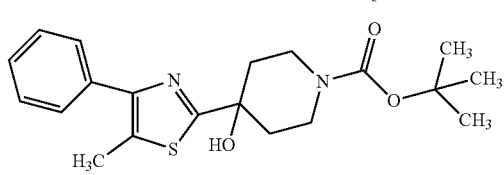

In place of 2-bromo-4-phenylthiazole in Example 1, 2-bromo-4-phenyl-5-methylthiazole was subjected to the operations according to Example 1 to give the title compound having the following physical properties.

TLC: Rf 0.56 (hexane:ethyl acetate=1:1);

$^1$H-NMR (CDCl$_3$): δ 7.65-7.58 (m, 2H), 7.47-7.29 (m, 3H), 4.10-3.87 (m, 2H), 3.39-3.23 (m, 2H), 3.22 (s, 1H), 2.55 (s, 3H), 2.08 (dt, J=4.8, 13.5 Hz, 2H), 1.93-1.80 (m, 2H), 1.48 (s, 9H).

Example 9

4-(5-Methyl-4-phenyl-1,3-thiazol-2-yl)-4-piperidinol

[Chemical Formula 23]

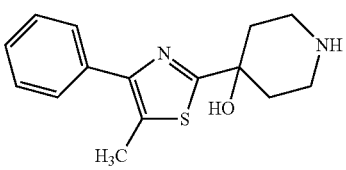

The compound produced in Example 8 (734 mg) was dissolved in methylene chloride (5 mL), and trifluoroacetic acid (3 mL) was added and the mixture was stirred at room temperature overnight. A 2N aqueous sodium hydroxide solution (20 mL) was added to the reaction solution, followed by extraction twice with methylene chloride (30 mL). The organic layer was washed with saturated saline (20 mL) and then dried using anhydrous sodium sulfate to give the title compound (537 mg) having the following physical properties.

TLC: Rf 0.22 (methanol:28% aqueous ammonia solution=20:1);

$^1$H-NMR (CDCl$_3$): δ 7.68-7.60 (m, 2H), 7.48-7.28 (m, 3H), 3.23-3.00 (m, 5H), 2.56 (s, 3H), 2.15 (dt, 2H), 1.98-1.84 (m, 2H).

Example 10

4-Hydroxy-4-(5-methyl-4-phenyl-1,3-thiazol-2-yl)-N-[4-(trifluoromethyl)phenyl]-1-piperidinecarboxamide The compound produced in Example 9 (100 mg) was dissolved in methylene chloride (15 mL), and 4-(trifluoromethyl)phenyl isocyanate (72 mg) was added and stirred at 0° C. for 1 hour. The reaction solution was concentrated under reduced pressure, and the resulting residue was purified by silica gel column chromatography (hexane:ethyl acetate=1:1) to give the obtained title compound (140 mg) having the following physical properties.

TLC: Rf 0.52 (hexane:ethyl acetate=1:1);
$^1$H-NMR (CDCl$_3$): δ 7.64 (d, J=8.4 Hz, 2H), 7.55 (d, J=9.0 Hz, 2H), 7.49 (d, J=9.0 Hz, 2H), 7.42 (t, J=8.4 Hz, 2H), 7.40-7.32 (m, 1H), 6.57 (s, 1H), 4.07-3.95 (m, 2H), 3.58-3.45 (m, 2H), 3.36 (s, 1H), 2.57 (s, 3H), 2.19 (dt, J=4.8 Hz, 13.8 Hz, 2H), 2.05-1.93 (m, 2H).

Example 11 (1) to Example 11 (3)

In place of 2-bromo-1-phenylpropan-1-one in Example 6, raw materials having corresponding functional groups were subjected to the operations according to the methods of Example 6→Example 7→Example 8→Example 9→Example 10 to give the following compounds.

Example 11 (1)

4-(5-Ethyl-4-phenyl-1,3-thiazol-2-yl)-4-hydroxy-N-[4-(trifluoromethyl)phenyl]-1-piperidinecarboxamide TLC: Rf 0.36 (hexane:acetate=1:1);
$^1$H-NMR (DMSO-d$_6$): δ 8.91 (s, 1H), 7.68 (d, J=8.7 Hz, 2H), 7.60-7.51 (m, 2H), 7.42 (t, J=7.8 Hz, 2H), 7.38-7.29 (m, 2H), 6.14 (s, 1H), 4.08-3.96 (m, 2H), 3.40-3.20 (m, 2H), 2.92 (q, J=7.5 Hz, 2H), 2.13-1.98 (m, 2H), 1.84-1.73 (m, 2H), 1.26 (t, 7.5 Hz, 3H).

Example 11 (2)

Ethyl 2-(4-hydroxy-1-{[4-(trifluoromethyl)phenyl]carbamoyl}-4-piperidinyl)-4-phenyl-1,3-thiazole-5-carboxylate TLC: Rf 0.38 (hexane:acetate=1:1):
$^1$H-NMR (DMSO-d$_6$): δ 7.78-7.68 (m, 2H), 7.54 (d, J=8.4 Hz, 2H), 7.47 (m, J=8.4 Hz, 2H), 7.46-7.36 (m, 3H), 6.53 (s, 1H), 4.28 (q, J=6.9 Hz, 2H), 4.10-4.00 (m, 2H), 3.56-3.40 (m, 2H), 3.07 (s, 1H), 2.34-2.20 (m, 2H), 2.04-1.92 (m, 2H), 1.28 (t, J=6.9 Hz, 3H).

Example 11 (3)

Ethyl 4-(2-fluorophenyl)-2-(4-hydroxy-1-{[4-(trifluoromethyl)phenyl]carbamoyl}-4-piperidinyl)-1,3-thiazole-5-carboxylate TLC: Rf 0.40 (hexane:acetate=1:1);
$^1$H-NMR (CDCl$_3$): δ 7.54 (d, J=8.7 Hz, 2H), 7.47 (d, J=8.7 Hz, 2H), 7.50-7.40 (m, 2H), 7.30-7.10 (m, 2H), 6.55 (s, 1H), 4.26 (q, J=7.2 Hz, 2H), 4.10-4.00 (m, 2H), 3.60-3.40 (m, 2H), 3.02 (s, 1H), 2.40-2.20 (m, 2H), 2.10-1.90 (m, 2H), 1.24 (t, J=7.2 Hz, 3H).

Example 12

4-Hydroxy-4-[5-(hydroxymethyl)-4-phenyl-1,3-thiazol-2-yl]-N-[4-(trifluoromethyl)phenyl]-1-piperidinecarboxamide The compound produced in Example 11 (2) (70 mg) was dissolved in tetrahydrofuran (3 mL), and lithium borohydride (15 mg) was added at 0° C. and the mixture was stirred at room temperature overnight. 1N hydrochloric acid (3 mL) and water (20 mL) were added to the reaction solution, followed by extraction twice with ethyl acetate (20 mL). The organic layer was washed with saturated saline (20 mL), then dried using anhydrous sodium sulfate, and concentrated under reduced pressure. The resulting residue was purified by silica gel column chromatography (hexane:ethyl acetate=1:1) to give the title compound (59 mg) having the following physical properties.

TLC: Rf 0.56 (hexane:acetate=1:1);
$^1$H-NMR (DMSO-d$_6$): δ 8.93 (s, 1H), 7.68 (d, J=8.7 Hz, 2H), 7.62 (d, J=7.5 Hz, 2H), 7.56 (d, J=8.7 Hz, 2H), 7.43 (t, J=7.5 Hz, 2H), 7.40-7.30 (m, 1H), 6.18 (s, 1H), 5.73 (t, J=5.4 Hz, 1H), 4.70 (d, J=5.4 Hz, 2H), 4.10-3.96 (m, 2H), 3.35-3.20 (m, 2H), 2.15-2.00 (m, 2H), 1.86-1.72 (m, 2H).

Example 13

4-[4-(2-Fluorophenyl)-5-(hydroxymethyl)-1,3-thiazol-2-yl]-4-hydroxy-N-[4-(trifluoromethyl)phenyl]-1-piperidinecarboxamide The compound produced in Example 11 (3) was subjected to the operations according to the method of Example 12 to give the title compound having the following physical properties.

TLC: Rf 0.39 (hexane:acetate=1:2);
$^1$H-NMR (DMSO-d$_6$): δ 8.91 (s, 1H), 7.67 (d, J=8.4 Hz, 2H), 7.55 (d, J=8.4 Hz, 2H), 7.60-7.40 (m, 2H), 7.30-7.20 (m, 2H), 6.20 (s, 1H), 5.61 (t, J=5.1 Hz, 1H), 4.51 (d, J=5.1 Hz, 2H), 4.15-4.00 (m, 2H), 3.30-3.20 (m, 2H), 2.10-2.00 (m, 2H), 1.90-1.70 (m, 2H).

Example 14

2-Methyl-2-propanil 4-fluoro-4-(5-methyl-4-phenyl-1,3-thiazol-2-yl)-1-piperidinecarboxylate

[Chemical Formula 24]

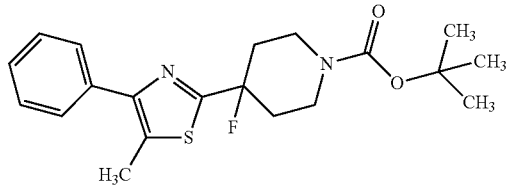

The compound produced in Example 8 (166 mg) was dissolved in methylene chloride (2 mL), and (diethylamino)sulfur trifluoride (107 mg) was added at −78° C. and the mixture was stirred for 30 minutes. Subsequently, stirring was further performed at room temperature for 2 hours. An aqueous saturated sodium hydrogen carbonate solution (20 mL) was added to the reaction solution, followed by extraction twice with ethyl acetate (20 mL). The organic layer was washed with saturated saline (20 mL), then dried using anhydrous sodium sulfate, and concentrated under reduced pressure. The resulting residue was purified by silica gel column chromatography (hexane:ethyl acetate=7:3) to give the title compound (144 mg) having the following physical properties.

¹H-NMR (CDCl₃): δ 7.64-7.57 (m, 2H), 7.48-7.28 (m, 3H), 4.18-3.94 (m, 2H), 3.34-3.15 (m, 2H), 2.57 (s, 3H), 2.43-2.00 (m, 4H), 1.47 (s, 9H).

Example 15

4-Fluoro-4-(5-methyl-4-phenyl-1,3-thiazol-2-yl)piperidine

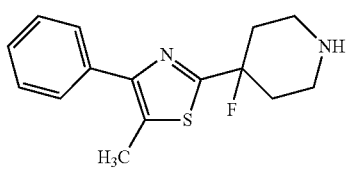

[Chemical Formula 25]

The compound produced in Example 14 (144 mg) was dissolved in methylene chloride (5 mL), and trifluoroacetic acid (0.28 mL) was added and the mixture was stirred at room temperature overnight. A 2N aqueous sodium hydroxide solution (10 mL) was added to the reaction solution, followed by extraction twice with methylene chloride (10 mL). The organic layer was washed with saturated saline (20 mL) and then dried using anhydrous sodium sulfate. The solvent was distilled off under reduced pressure to give the title compound (105 mg) having the following physical properties.
TLC: Rf 0.25 (methanol:28% aqueous ammonia solution=20:1);
¹H-NMR (CDCl₃): δ 7.68-7.60 (m, 2H), 7.46-7.28 (m, 3H), 3.15-3.00 (m, 4H), 2.56 (s, 3H), 2.20-2.04 (m, 4H).

Example 16

4-Fluoro-4-(5-methyl-4-phenyl-1,3-thiazol-2-yl)-N-[4-(trifluoromethyl)phenyl]-1-piperidinecarboxamide The compound produced in Example 15 was subjected to the operations according to the method of Example 10 to give the title compound having the following physical properties.
TLC: Rf 0.25 (hexane:acetate=3:1);
¹H-NMR (CDCl₃): δ 7.65-7.58 (m, 2H), 7.54 (d, J=9.0 Hz, 2H), 7.50-7.30 (m, 5H), 6.57 (s, 1H), 4.10-4.00 (m, 2H), 3.52-3.40 (m, 2H), 2.58 (s, 3H), 2.54-2.18 (m, 4H).

Example 17

2-Methyl-2-propanil 4-(4-bromo-1,3-thiazol-2-yl)-4-hydroxy-1-piperidinecarboxylate

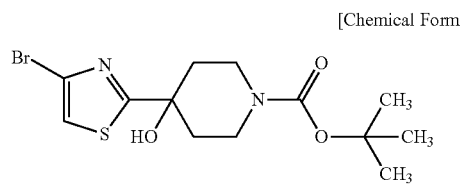

[Chemical Formula 26]

2,4-Dibromothiazole (5.0 g) was dissolved in methylene chloride (40 mL), and n-butyllithium (1.6N hexane solution, 14.2 mL) was slowly added dropwise at −78° C. and the mixture was stirred for 20 minutes. 1-(tert-Butoxycarbonyl)-4-piperidinone (4.1 g) was added thereto and then the resulting mixture was stirred at room temperature for 15 minutes. The reaction liquid was charged into an aqueous saturated ammonium chloride solution (100 mL), followed by extraction twice with methylene chloride (50 mL). The organic layer was dried over anhydrous sodium sulfate and concentrated under reduced pressure. The resulting residue was purified by silica gel column chromatography (hexane:ethyl acetate=7:3 to 1:1). The resulting compound (6.5 g) was dissolved in ethyl acetate, and hexane was added. The resulting crystals were collected by filtration, washed with hexane, and then dried at room temperature under reduced pressure to give the title compound (5.03 g) having the following physical properties.
TLC: Rf 0.09 (hexane:ethyl acetate=4:1);
¹H-NMR (CDCl₃): δ 1.46 (s, 9H), 1.76-1.86 (m, 2H), 2.14 (td, 12.3, 4.8 Hz, 2H), 2.77 (s, 1H), 3.20-3.34 (m, 2H), 3.93-4.14 (m, 2H), 7.18 (s, 1H).

Example 18

4-(4-Bromo-1,3-thiazol-2-yl)-4-piperidinol trifluoroacetate

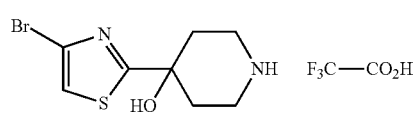

[Chemical Formula 27]

The compound produced in Example 17 (2.0 g) was dissolved in methylene chloride (40 mL), and trifluoroacetate (2 mL) was added. After the mixture was stirred at room temperature for 1 hour, trifluoroacetic acid (2 mL) was added thereto. After further stirring for 10 minutes, the reaction liquid was concentrated under reduced pressure to give the title compound (1.44 g) having the following physical properties.
¹H-NMR (CDCl₃): δ 2.15-2.26 (m, 2H), 2.36-2.51 (m, 2H), 2.78-2.84 (m, 1H), 3.52-3.68 (m, 4H), 7.26 (s, 1H).

Example 19

4-(4-Bromo-1,3-thiazol-2-yl)-4-hydroxy-N-[4-(trifluoromethyl)phenyl]-1-piperidinecarboxamide

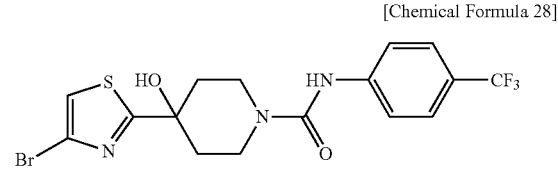 [SMILES: O=C(Nc1ccc(C(F)(F)F)cc1)N1CCC(O)(c2nc(Br)cs2)CC1]

[Chemical Formula 28]

The compound produced in Example 18 was dissolved in methylene chloride (10 mL), and diisopropylethylamine (2.86 mL) and 4-(trifluoromethyl)phenyl isocyanate (1.03 g) were added under ice-cooling. After stirring at room temperature for 70 minutes, the reaction solution was charged into an aqueous saturated ammonium chloride solution (30 mL), followed by extraction twice with ethyl acetate (20 mL). The organic layer was dried over anhydrous sodium sulfate and concentrated under reduced pressure. The resulting residue was purified by silica gel column chromatography (hexane:ethyl acetate=7:3 to 3:7) to give the title compound (1.53 g) having the following physical properties.

TLC: Rf 0.51 (hexane:ethyl acetate=3:7);
$^1$H-NMR (DMSO-$d_6$): δ 1.68-1.79 (m, 2H), 1.92-2.05 (m, 2H), 3.15-3.27 (m, 2H), 3.98-4.08 (m, 2H), 6.36 (s, 1H), 7.56 (d, J=8.7 Hz, 2H), 7.68 (d, J=8.7 Hz, 2H), 7.72 (s, 1H), 8.92 (s, 1H).

Example 20

4-Hydroxy-4-[4-(6-isopropoxy-3-pyridyl)-1,3-thiazol-2-yl]-N-[4-(trifluoromethyl)phenyl]-1-piperidinecarboxamide The compound produced in Example 19 (150 mg), tetrakis(triphenylphosphine)palladium (38.5 mg), (6-isopropoxy-3-pyridyl)boric acid (65 mg), and tripotassium phosphate (212 mg) were dissolved in 1,4-dioxane (4 mL) and the mixture was stirred at 90° C. overnight. The reaction solution was added to water (10 mL), followed by extraction with ethyl acetate (20 mL). The organic layer was dried over anhydrous sodium sulfate and concentrated under reduced pressure. The resulting residue was purified by silica gel column chromatography (hexane:ethyl acetate=7:3 to 3:7) to give the title compound (89.5 mg) having the following physical properties.

$^1$H-NMR (CDCl$_3$): δ 8.66 (dd, J=2.6, 0.7 Hz, 1H), 8.02 (dd, J=8.6, 2.6 Hz, 1H), 7.57-7.42 (m, 4H), 7.34 (s, 1H), 6.82 (s, 1H), 6.73 (dd, J=8.6, 0.7 Hz, 1H), 5.32 (quin, J=6.2 Hz, 1H), 4.08-3.98 (m, 2H), 3.62-3.45 (m, 3H), 2.25 (td, J=12.7, 4.5 Hz, 2H), 2.07-1.92 (m, 2H), 1.35 (d, J=6.3 Hz, 6H).

Example 21 (1) to Example 21 (4)

In place of (6-isopropoxy-3-pyridyl)boric acid of Example 20, corresponding aryl boric acids were subjected to the operations according to Example 20 to give the following compounds.

Example 21 (1)

4-[4-(4-Cyanophenyl)-1,3-thiazol-2-yl]-4-hydroxy-N-[4-(trifluoromethyl)phenyl]-1-piperidinecarboxamide TLC: Rf 0.52 (hexane:acetate=1:3);
$^1$H-NMR (DMSO-$d_6$): δ 8.94 (s, 1H), 8.28 (s, 1H), 8.11 (d, J=8.7 Hz, 2H), 7.87 (d, J=8.7 Hz, 2H), 7.70 (d, J=8.7 Hz, 2H), 7.57 (d, J=8.7 Hz, 2H), 6.32 (s, 1H), 4.12-3.94 (m, 2H), 3.40-3.20 (m, 2H), 2.18-2.00 (m, 2H), 1.87-1.73 (m, 2H).

Example 21 (2)

4-Hydroxy-4-[4-(3-methylphenyl)-1,3-thiazol-2-yl]-N-[4-(trifluoromethyl)phenyl]-1-piperidinecarboxamide TLC: Rf 0.45 (hexane:acetate=1:2);
$^1$H-NMR (CDCl$_3$): δ 7.71 (s, 1H), 7.66 (d, J=7.5 Hz, 1H), 7.54 (d, J=9.0 Hz, 2H), 7.49 (d, J=9.0 Hz, 2H), 7.43 (s, 1H), 7.30 (t, J=7.5 Hz, 2H), 7.15 (d, J=7.5 Hz, 1H), 6.57 (s, 1H), 4.09-3.98 (m, 2H), 3.60-3.46 (m, 2H), 3.24 (s, 1H), 2.41 (s, 3H), 2.34-2.19 (m, 2H), 2.07-1.96 (m, 2H).

Example 21 (3)

4-Hydroxy-4-[4-(2-methoxyphenyl)-1,3-thiazol-2-yl]-N-[4-(trifluoromethyl)phenyl]-1-piperidinecarboxamide TLC: Rf 0.42 (hexane:acetate=1:);
$^1$H-NMR (CDCl$_3$): δ 8.23 (dd, J=7.5, 1.5 Hz, 1H), 7.92 (s, 1H), 7.55 (d, J=8.7 Hz, 2H), 7.50 (d, J=8.7 Hz, 2H), 7.32 (dt, J=8.4, 1.8 Hz, 1H), 7.06 (t, J=7.5 Hz, 1H), 7.00 (d, J=8.4 Hz, 1H), 6.57 (s, 1H), 4.08-3.98 (m, 2H), 3.96 (s, 3H), 3.61-3.46 (m, 2H), 3.32 (s, 1H), 2.48 (dt, J=13.2, 4.5 Hz, 2H), 2.06-1.95 (m, 2H).

Example 21 (4)

4-[4-(4-Fluorophenyl-1,3-thiazol-2-yl]-4-hydroxy-N-[4-(trifluoromethyl)phenyl]-1-piperidinecarboxamide TLC: Rf 0.63 (hexane:acetate=1:2);
$^1$H-NMR (CDCl$_3$): δ 7.85 (dd, J=9.0, 5.4 Hz, 2H), 7.54 (d, J=9.0 Hz, 2H), 7.49 (d, J=9.0 Hz, 2H), 7.39 (s, 1H), 7.10 (t, J=9.0 Hz, 2H), 6.57 (s, 1H), 4.10-3.98 (m, 2H), 3.60-3.45 (m, 2H), 3.18 (d, 1H), 2.32-2.20 (m, 2H), 2.08-1.95 (m, 2H).

Example 22

2,4-Dibromo-5-methyl-1,3-thiazole

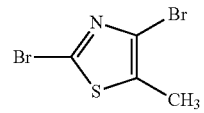

[Chemical Formula 29]

2-Amino-5-methylthiazole (10 g) was dissolved in phosphoric acid (100 mL) and nitric acid (50 mL), and an aqueous solution (40 mL) of sodium nitrite (19 g) was slowly added dropwise under ice-cooling over about 30 minutes. After stirring for 20 minutes on an ice bath, the solution was added to a suspension solution of copper bromide (13 g) suspended in a hydrobromic acid/acetic acid solution (60 mL) and water (30 mL) over 30 minutes, and the mixture was stirred at room temperature for 3 hours. A 2N aqueous sodium hydroxide solution was added to the reaction liquid for neutralization, followed by extraction twice with ethyl acetate (200 mL). The organic layer was washed with saturated saline (200 mL), then dried using anhydrous magnesium sulfate, and concentrated under reduced pressure. The resulting residue was washed with hexane to give the title compound (13 g) having the following physical properties.

TLC: Rf 0.75 (hexane:ethyl acetate=3:1);
$^1$H-NMR (CDCl$_3$): δ 2.36 (s, 3H).

Example 23

2-Methyl-2-propanil 4-(4-bromo-5-methyl-1,3-thiazol-2-yl)-4-hydroxy-1-piperidinecarboxylate

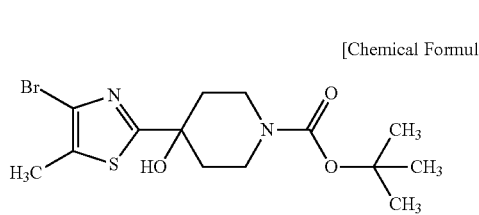

[Chemical Formula 30]

The compound produced in Example 22 (3.51 g) was dissolved in methylene chloride (40 mL), and n-butyllithium (1.60M hexane solution, 8.5 mL) was added at −78° C. and the mixture was stirred for 30 minutes. Subsequently, 1-(tert-butoxycarbonyl)-4-piperidone (2.72 g) was added at −78° C. and the resulting mixture was stirred for 15 minutes. An aqueous saturated ammonium chloride solution (100 mL) was added to the reaction solution, followed by extraction twice with methylene chloride (100 mL). The organic layer was washed with saturated saline (100 mL), then dried using anhydrous sodium sulfate, and concentrated under reduced pressure. The resulting residue was purified by silica gel column chromatography (hexane:ethyl acetate=1:1) to give the title compound (5.1 g) having the following physical properties.

TLC: Rf 0.40 (hexane:ethyl acetate=3:1);

$^1$H-NMR (CDCl$_3$): δ 4.15-3.86 (m, 2H), 3.31-3.13 (m, 2H), 2.65 (s, 1H), 2.38 (s, 3H), 2.09 (dt, J=4.8, 13.5 Hz, 2H), 1.85-1.73 (m, 2H), 1.47 (s, 9H).

Example 24

4-(4-Bromo-5-methyl-1,3-thiazol-2-yl)-4-piperidinol

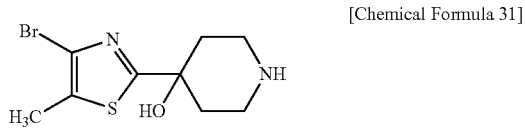

[Chemical Formula 31]

The compound produced in Example 23 (5.1 g) was dissolved in methylene chloride (10 mL), and trifluoroacetic acid (10 mL) was added and the mixture was stirred at room temperature for 3 hours. A 5N aqueous sodium hydroxide solution (30 mL) was added to the reaction solution, and precipitated crystals were collected by filtration. The crystals were dried under reduced pressure to give the title compound (2.85 g) having the following physical properties.

TLC: Rf 0.37 (methanol:28% aqueous ammonia solution=20:1);

$^1$H-NMR (DMSO-d$_6$): δ 5.92 (s, 1H), 4.03 (s, 1H), 2.87-2.68 (m, 4H), 2.31 (s, 3H), 1.85 (dt, J=4.8, 13.2 Hz, 2H), 1.60-1.50 (m, 2H).

Example 25

4-(4-Bromo-5-methyl-1,3-thiazol-2-yl)-4-hydroxy-N-[4-(trifluoromethyl)phenyl]-1-piperidinecarboxamide

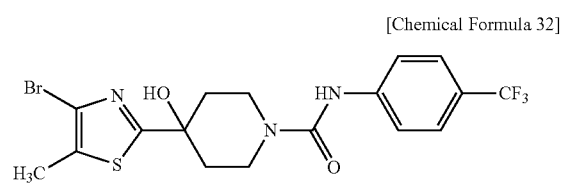 [SMILES: Cc1sc(C2(O)CCN(C(=O)Nc3ccc(C(F)(F)F)cc3)CC2)nc1Br]

[Chemical Formula 32]

The compound produced in Example 24 was subjected to the operations according to the method of Example 10 to give the title compound having the following physical properties.

TLC: Rf 0.37 (hexane:ethyl acetate=1:1);

$^1$H-NMR (CDCl$_3$): δ 8.91 (s, 1H), 7.67 (d, J=8.4 Hz, 2H), 7.56 (d, J=8.4 Hz, 2H), 6.27 (s, 1H), 4.10-3.90 (m, 2H), 3.40-3.13 (m, 2H), 2.33 (s, 3H), 2.02-1.85 (m, 2H), 1.78-1.63 (m, 2H).

Example 26

4-[4-(2-Fluorophenyl)-5-methyl-1,3-thiazol-2-yl]-4-hydroxy-N-[4-(trifluoromethyl)phenyl]-1-piperidinecarboxamide The compound produced in Example 25 (100 mg), 2-fluorophenylboronic acid (45 mg), and tetrakis(triphenylphosphine)palladium (15 mg) were suspended in 1,4-dioxane (2 mL) and an aqueous potassium phosphate solution (2M, 0.2 mL), and the mixture was stirred at 100° C. for 45 minutes under irradiation with microwaves (manufactured by Biotage Ltd.). The reaction liquid was concentrated under reduced pressure. The resulting residue was purified by amino silica gel column chromatography (hexane:ethyl acetate=7:3) to give the title compound (95 mg) having the following physical properties.

TLC: Rf 0.52 (hexane:acetate=1:1);

$^1$H-NMR (CDCl$_3$): δ 8.90 (s, 1H), 7.67 (d, J=8.4 Hz, 2H), 7.55 (d, J=8.4 Hz, 2H), 7.52-7.36 (m, 2H), 7.34-7.20 (m, 2H), 6.17 (s, 1H), 4.08-3.91 (m, 2H), 3.40-3.30 (m, 2H), 2.32 (s, 3H), 2.12-1.96 (m, 2H), 1.85-1.72 (m, 2H).

Example 27 (1) to Example 27 (10)

In place of 2-fluorophenylboronic acid of Example 26, corresponding aryl boric acids were subjected to the operations according to Example 26 to give the following compounds.

Example 27 (1)

4-[4-(3-Fluorophenyl)-5-methyl-1,3-thiazol-2-yl]-4-hydroxy-N-[4-(trifluoromethyl)phenyl]-1-piperidinecarboxamide

[Chemical Formula 33]

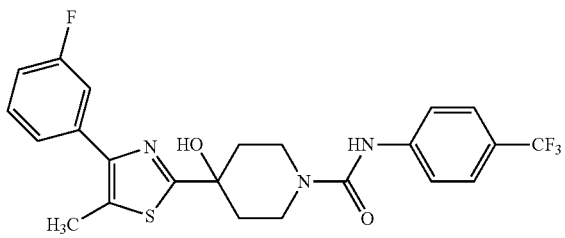

TLC: Rf 0.50 (hexane:acetate=1:1);
¹H-NMR (CDCl₃): δ 8.91 (s, 1H), 7.68 (d, J=8.7 Hz, 2H), 7.56 (d, J=8.7 Hz, 2H), 7.52-7.38 (m, 3H), 7.21-7.09 (m, 1H), 6.17 (s, 1H), 4.10-3.94 (m, 2H), 3.40-3.30 (m, 2H), 2.54 (s, 3H), 2.12-1.98 (m, 2H), 1.84-1.71 (m, 2H).

Example 27 (2)

4-[4-(4-Fluorophenyl-5-methyl-1,3-thiazol-2-yl]-4-hydroxy-N-[4-(trifluoromethyl)phenyl]-1-piperidinecarboxamide TLC: Rf 0.50 (hexane:acetate=1:1);
¹H-NMR (DMSO-d₆): δ 8.91 (s, 1H), 7.73-7.62 (m, 4H), 7.56 (d, J=8.7 Hz, 2H), 7.24 (t, J=9.0 Hz, 2H), 6.14 (s, 1H), 4.08-3.94 (m, 2H), 3.40-3.30 (m, 2H), 2.49 (s, 3H), 2.12-1.96 (m, 2H), 1.84-1.72 (m, 2H).

Example 27 (3)

4-[4-(2-Cyanophenyl)-5-methyl-1,3-thiazol-2-yl]-4-hydroxy-N-[4-(trifluoromethyl)phenyl]-1-piperidinecarboxamide TLC: Rf 0.35 (hexane:acetate=1:1);
¹H-NMR (DMSO-d₆): δ 8.92 (s, 1H), 7.92 (d, J=8.4 Hz, 1H), 7.80-7.48 (m, 7H), 6.22 (s, 1H), 4.08-3.92 (m, 2H), 3.40-3.20 (m, 2H), 2.44 (s, 3H), 2.14-2.00 (m, 2H), 2.84-1.70 (m, 2H).

Example 27 (4)

4-[4-(3-Cyanophenyl)-5-methyl-1,3-thiazol-2-yl]-4-hydroxy-N-[4-(trifluoromethyl)phenyl]-1-piperidinecarboxamide TLC: Rf 0.38 (hexane:acetate=1:1);
¹H-NMR (DMSO-d₆): δ 8.91 (s, 1H), 8.05 (s, 1H), 7.98 (d, J=8.4 Hz, 1H), 7.80 (d, J=7.5 Hz, 1H), 7.72-7.60 (m, 3H), 7.56 (d, J=8.7 Hz, 2H), 6.20 (s, 1H), 4.08-3.96 (m, 2H), 3.40-3.20 (m, 2H), 2.56 (s, 3H), 2.15-2.00 (m, 2H), 1.84-1.73 (m, 2H).

Example 27 (5)

4-[4-(4-Cyanophenyl)-5-methyl-1,3-thiazol-2-yl]-4-hydroxy-N-[4-(trifluoromethyl)phenyl]-1-piperidinecarboxamide TLC: Rf 0.35 (hexane:acetate=1:1);
¹H-NMR (DMSO-d₆): δ 8.92 (s, 1H), 7.92-7.80 (m, 4H), 7.68 (d, J=8.4 Hz, 2H), 7.56 (d, J=8.4 Hz, 2H), 6.21 (s, 1H), 4.10-3.92 (m, 2H), 3.40-3.20 (m, 2H), 2.57 (s, 3H), 2.13-2.00 (m, 2H), 1.85-1.72 (m, 2H).

Example 27 (6)

4-Hydroxy-4-[4-(2-methoxyphenyl)-5-methyl-1,3-thiazol-2-yl]-N-[4-(trifluoromethyl)phenyl]-1-piperidinecarboxamide TLC: Rf 0.46 (hexane:acetate=1:1);
¹H-NMR (DMSO-d₆): δ 8.89 (s, 1H), 7.66 (d, J=8.7 Hz, 2H), 7.54 (d, J=8.7 Hz, 2H), 7.35 (dt, J=8.1, 1.8 Hz, 1H), 7.27 (dd, J=7.5, 1.8 Hz, 1H), 7.08 (d, J=8.1 Hz, 1H), 6.97 (t, J=7.5 Hz, 1H), 6.07 (s, 1H), 4.06-3.92 (m, 2H), 3.75 (s, 3H), 3.40-3.20 (m, 2H), 2.21 (s, 3H), 2.09-1.93 (m, 2H), 1.84-1.72 (m, 2H).

Example 27 (7)

4-Hydroxy-4-[4-(3-methoxyphenyl)-5-methyl-1,3-thiazol-2-yl]-N-[4-(trifluoromethyl)phenyl]-1-piperidinecarboxamide TLC: Rf 0.48 (hexane:acetate=1:1);
¹H-NMR (DMSO-d₆): δ 8.91 (s, 1H), 7.68 (d, J=8.7 Hz, 2H), 7.56 (d, J=8.7 Hz, 2H), 7.34 (t, J=7.5 Hz, 1H), 7.19 (d, J=7.5 Hz, 1H), 7.14 (d, J=2.4 Hz, 1H), 6.91 (dd, J=7.5, 2.4 Hz, 1H), 6.13 (s, 1H), 4.08-3.95 (m, 2H), 3.77 (s, 3H), 3.40-3.30 (m, 2H), 2.51 (s, 3H), 2.12-2.00 (m, 2H), 2.04-1.72 (m, 2H).

Example 27 (8)

4-Hydroxy-4-[4-(4-methoxyphenyl)-5-methyl-1,3-thiazol-2-yl]-N-[4-(trifluoromethyl)phenyl]-1-piperidinecarboxamide TLC: Rf 0.48 (hexane:acetate=1:1);
¹H-NMR (CDCl₃): δ 7.60-7.44 (m, 6H), 7.00-6.93 (m, 2H), 6.59 (s, 1H), 4.06-3.94 (m, 2H), 3.85 (s, 3H), 3.56-3.43 (m, 2H), 3.40 (s, 1H), 2.54 (s, 3H), 2.24-2.10 (m, 2H), 2.02-1.90 (m, 2H).

Example 27 (9)

4-Hydroxy-4-[5-methyl-4-(3-pyridyl)-1,3-thiazol-2-yl]-N-[4-(trifluoromethyl)phenyl]-1-piperidinecarboxamide TLC: Rf 0.58 (acetate);
H-NMR (CDCl₃): δ 8.92 (s, 1H), 8.84 (d, J=1.5 Hz, 1H), 8.52 (dd, J=1.5, 4.5 Hz, 1H), 8.02 (dt, J=1.5, 7.5 Hz, 1H), 7.67 (d, J=8.7 Hz, 2H), 7.55 (d, J=8.7 Hz, 2H), 7.44 (dd, J=4.5, 7.5 Hz, 1H), 6.20 (s, 1H), 4.08-3.95 (m, 2H), 3.40-3.20 (m, 2H), 2.55 (s, 3H), 2.12-2.00 (m, 2H), 1.86-1.72 (m, 2H).

Example 27 (10)

4-Hydroxy-4-[5-methyl-4-(4-pyridyl)-1,3-thiazol-2-yl]-N-[4-(trifluoromethyl)phenyl]-1-piperidinecarboxamide TLC: Rf 0.44 (acetate);
$^1$H-NMR (CDCl$_3$): δ 8.92 (s, 1H), 8.60 (d, J=6.0 Hz, 2H), 7.68 (d, J=9.0 Hz, 2H), 7.65 (d, J=6.0 Hz, 2H), 7.56 (d, J=9.0 Hz, 2H), 6.22 (s, 1H), 4.08-3.96 (m, 2H), 3.40-3.20 (m, 2H), 2.60 (s, 3H), 2.12-2.00 (m, 2H), 1.84-1.72 (m, 2H).

Example 28

4-(4-Bromo-5-methyl-1,3-thiazol-2-yl)-N-[4-(trifluoromethyl)phenyl]-1-piperidinecarboxamide

[Chemical Formula 34]

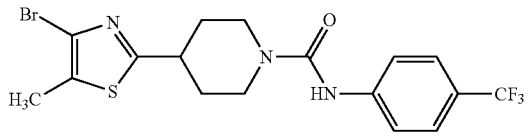

The compound produced in Example 25 (2.2 g) was dissolved in trifluoroacetic acid (30 mL), and triethylsilane (7 mL) was added and the mixture was stirred at 50° C. for 15 hours. A 2N aqueous sodium hydroxide solution (20 mL) was added to the reaction solution, followed by extraction twice with methylene chloride (20 mL). The organic layer was washed with saturated saline (20 mL), then dried using anhydrous sodium sulfate, and concentrated under reduced pressure. The resulting residue was purified by silica gel column chromatography (hexane:ethyl acetate=7:3) to give the title compound (713 mg) having the following physical properties.

TLC Rf; 0.76 (hexane:ethyl acetate=1:1);
$^1$H-NMR (CDCl$_3$): δ 7.53 (d, J=8.7 Hz, 2H), 7.46 (d, J=8.7 Hz, 2H), 6.52 (s, 1H), 4.20-4.08 (m, 2H), 3.16 (tt, J=3.9, 11.1 Hz, 1H), 3.15-3.06 (m, 2H), 2.37 (s, 3H), 2.21-2.10 (m, 2H), 1.90-1.72 (m, 2H).

Example 29 (1) to Example 29 (3)

The compound produced in Example 28 and corresponding aryl boric acids were subjected to the operations according to Example 26 to give the following compounds.

Example 29 (1)

4-[4-(2-Fluorophenyl-5-methyl-1,3-thiazol-2-yl]-N-[4-(trifluoromethyl)phenyl]-1-piperidinecarboxamide TLC: Rf 0.54 (hexane:acetate=1:1);
$^1$H-NMR (CDCl$_3$): δ 7.58-7.40 (m, 5H), 7.40-7.28 (m, 1H), 7.28-7.05 (m, 2H), 6.59 (s, 1H), 4.24-4.09 (m, 2H), 3.30-3.16 (m, 1H), 3.16-3.00 (m, 2H), 2.37 (s, 3H), 2.27-2.13 (m, 2H), 1.95-1.75 (m, 2H).

Example 29 (2)

4-[4-(3-Fluorophenyl-5-methyl-1,3-thiazol-2-yl]-N-[4-(trifluoromethyl)phenyl]-1-piperidinecarboxamide

[Chemical Formula 35]

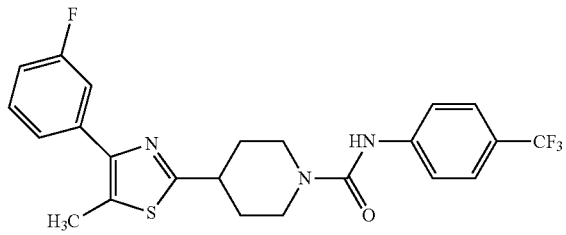

TLC: Rf 0.62 (hexane:acetate=1:1);
$^1$H-NMR (DMSO-d$_6$): δ 8.92 (s, 1H), 7.67 (d, J=9.0 Hz, 2H), 7.56 (d, J=9.0 Hz, 2H), 7.53-7.38 (m, 3H), 7.25-7.10 (m, 1H), 4.28-4.10 (m, 2H), 3.35-3.16 (m, 1H), 3.09-2.90 (m, 2H), 2.54 (s, 3H), 2.15-1.98 (m, 2H), 1.74-1.55 (m, 2H).

Example 29 (3)

4-[4-(4-Fluorophenyl-5-methyl-1,3-thiazol-2-yl]-N-[4-(trifluoromethyl)phenyl]-1-piperidinecarboxamide TLC: Rf 0.64 (hexane:acetate=1:1);
$^1$H-NMR (DMSO-d$_6$): δ 8.92 (s, 1H), 7.78-7.60 (m, 4H), 7.56 (d, J=8.7 Hz, 2H), 7.26 (t, J=9.0 Hz, 2H), 4.26-4.09 (m, 2H), 3.22 (tt, J=11.4, 3.6 Hz, 1H), 3.08-2.90 (m, 2H), 2.49 (s, 3H), 2.13-2.00 (m, 2H), 1.64 (dq, J=11.4, 3.6 Hz, 2H).

Example 30

2-Methyl-2-propanil 4-cyano-4-(4-phenyl-1,3-thiazol-2-yl)-1-piperidinecarboxylate

[Chemical Formula 36]

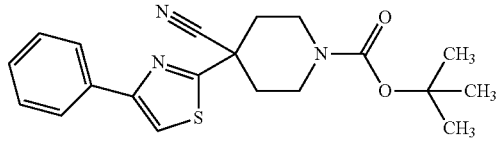

tert-Butyl 4-cyanopiperidine-1-carboxylate (600 mg) and 2-chloro-4-phenylthiazole (400 mg) were dissolved in tetrahydrofuran (5 mL), and lithium bis(trimethylsilyl)amide (1N, 3.4 mL) was added at −78° C. and the mixture was stirred for 15 minutes. Subsequently, the temperature was raised to room temperature, followed by stirring for 3 hours. An aqueous saturated ammonium chloride solution (30 mL) was added to the reaction solution, followed by extraction twice with ethyl acetate (30 mL). The organic layer was washed with saturated saline (30 mL), then dried using anhydrous sodium sulfate, and concentrated under reduced pressure. The resulting residue was purified by silica gel column chromatography (hexane:ethyl acetate=1:1) to give the title compound (800 mg) having the following physical properties.

TLC Rf 0.42 (hexane:ethyl acetate=3:1);
$^1$H-NMR (CDCl$_3$): δ 7.92-7.86 (m, 2H), 7.49 (s, 1H), 7.48-7.31 (m, 3H), 4.37-4.09 (m, 2H), 3.36-3.15 (m, 2H), 2.43-2.15 (m, 4H), 1.48 (s, 9H).

Example 31

4-(4-Phenyl-1,3-thiazol-2-yl)-4-piperidinecarbonitrile hydrochloride

[Chemical Formula 37]

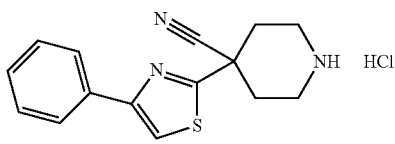

The compound produced in Example 30 (600 mg) was dissolved in 1,4-dioxane (3 mL), and a 4N hydrogen chloride/1,4-dioxane solution (3 mL) was added and the mixture was stirred at room temperature for 2 hours. The resulting crystals were collected by filtration and dried under reduced pressure to give the title compound (444 mg) having the following physical properties.
TLC Rf 0.28 (methanol: 28% aqueous ammonia=20:1);
$^1$H-NMR (DMSO-d$_6$): δ 9.29 (bs, 2H), 8.26 (s, 1H), 7.95 (d, J=7.5 Hz, 2H), 7.46 (t, J=7.5 Hz, 2H), 7.43-7.30 (m, 1H), 3.55-3.31 (m, 2H), 3.22-3.00 (m, 2H), 2.70-2.40 (m, 4H).

Example 32

4-Cyano-4-(4-phenyl-1,3-thiazol-2-yl)-N-[4-(trifluoromethyl)phenyl]-1-piperidinecarboxamide In place of 4-(4-phenyl-1,3-thiazol-2-yl)-4-piperidinol hydrochloride, the compound produced in Example 31 was subjected to the operations according to Example 3 to give the title compound having the following physical properties.
TLC: Rf 0.38 (hexane:acetate=2:1);
$^1$H-NMR (CDCl$_3$): δ 7.89 (d, J=8.4 Hz, 2H), 7.55 (d, J=8.7 Hz, 2H), 7.52-7.28 (m, 6H), 6.56 (s, 1H), 4.29-4.15 (m, 2H), 3.55-3.40 (m, 2H), 2.53-2.30 (m, 4H).

Example 33

2-Methyl-2-propanil 4-(5-methyl-4-phenyl-1,3-thiazol-2-yl)-1-piperidinecarboxylate

[Chemical Formula 38]

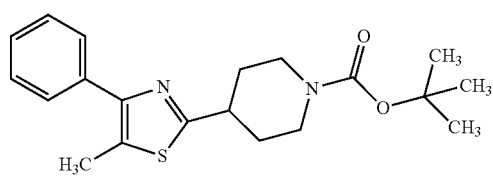

tert-Butyl 4-carbamothioylpiperidine-1-carboxylate (2.0 g) and potassium hydrogen carbonate (1.64 g) were added to a solution (20 mL) of 2-bromo-1-phenylpropan-1-one (1.92 g) in tetrahydrofuran and heated under reflux for 5 hours. After cooling to room temperature, the reaction solution was charged into water, followed by extraction with ethyl acetate. The organic layer was washed with saturated saline, dried over anhydrous sodium sulfate, and then concentrated. The resulting residue was purified by silica gel column chromatography (hexane:ethyl acetate=4:1) to give the title compound (1.89 g) having the following physical properties.
TLC Rf; 0.67 (hexane:acetate=2:1);
$^1$H-NMR (CDCl$_3$): δ 7.59-7.65 (m, 2H), 7.38-7.46 (m, 2H), 7.32 (m, 1H), 4.32-4.06 (m, 2H), 3.13 (tt, J=12.8, 3.8 Hz, 1H), 2.88 (t, J=12.8 Hz, 2H), 2.54 (s, 3H), 2.11 (dd, J=12.8, 2.2 Hz, 2H), 1.74 (dq, J=12.8, 3.8 Hz, 2H), 1.52-1.43 (m, 9H).

Example 34

4-(5-Methyl-4-phenyl-1,3-thiazol-2-yl)piperidine trifluoroacetate

[Chemical Formula 39]

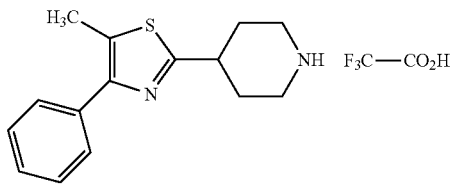

The compound produced in Example 33 (300 mg) was dissolved in methylene chloride (2 mL), and trifluoroacetic acid (2 mL) was added and the mixture was stirred at room temperature for 21 hours. Concentration was performed under reduced pressure to give a crude product (610 mg) of the title compound having the following physical properties.
$^1$H-NMR (CDCl$_3$): δ 7.55-7.39 (m, 5H), 3.86 (t, J=11.3 Hz, 1H), 3.63 (brd, J=12.4 Hz, 2H), 3.34-3.07 (m, 2H), 2.59 (s, 3H), 2.48-2.13 (m, 4H).

Example 35

4-(5-Methyl-4-phenyl-1,3-thiazol-2-yl)-N-[4-(trifluoromethyl)phenyl]-1-piperidinecarboxamide The compound produced in Example 34 (610 mg) was subjected to the method according to Example 32 to give the title compound (314 mg) having the following physical properties.
TLC: Rf 0.63 (hexane:acetate=1:1);
$^1$H-NMR (CDCl$_3$): δ 7.64-7.60 (m, 2H), 7.53 (d, J=9.0 Hz, 2H), 7.48 (d, J=9.0 Hz, 2H), 7.46-7.40 (m, 2H), 7.33 (tt, J=7.5, 0.9 Hz, 1H), 6.63 (brs, 1H), 4.17 (dt, J=13.5, 3.6 Hz, 2H), 3.23 (tt, J=11.7, 3.6 Hz, 1H), 3.10 (ddd, J=13.5, 11.7, 2.7 Hz, 2H), 2.54 (s, 3H), 2.21 (m, 2H), 1.87 (dq, J=11.7, 3.6 Hz, 2H).

Example 36

4-(5-Methyl-4-phenyl-1,3-thiazol-2-yl)-N-[5-(trifluoromethyl)-2-pyridyl]-1-piperidinecarboxamide 5-Trifluoromethylpyridin-2-amine (500 mg) was dissolved in methylene chloride (5 mL), and pyridine (268 mg)

and 4-nitrophenyl chloroformate (621 mg) were added and the mixture was stirred at room temperature for 30 minutes, and then crystals were collected by filtration. The crystals were dried under reduced pressure to give (4-nitrophenyl) N-[4-(trifluoromethyl)phenyl]carbamate (766 mg).

The compound (100 mg) produced in Example 34 was dissolved in a mixture of dimethylsulfoxide (2 mL) and triethylamine (0.14 mL). (4-Nitrophenyl) N-[4-(trifluoromethyl)phenyl]carbamate (133 mg) was added thereto and the mixture was stirred at 60° C. for 1 hour. The reaction solution was charged into water, followed by extraction with ethyl acetate. The organic layer was washed with saturated saline, dried over anhydrous sodium sulfate, and then concentrated. The resulting residue was purified by silica gel column chromatography (hexane:ethyl acetate=71:29 to 1:1) to give the title compound (93 mg) having the following physical properties.

TLC: Rf 0.50 (hexane:acetate=1:1);
$^1$H-NMR (CDCl$_3$): δ 8.45 (m, 1H), 8.17 (d, J=8.7 Hz, 1H), 7.85 (dd, J=8.7, 2.4 Hz, 1H), 7.63-7.59 (m, 2H), 7.47 (brs, 1H), 7.45-7.39 (m, 2H), 7.33 (m, 1H), 4.27-4.16 (m, 2H), 3.30-3.10 (m, 3H), 2.54 (s, 3H), 2.28-2.19 (m, 2H), 1.96-1.82 (m, 2H).

Examples 37 (1) to 37 (6)

In place of 2-bromo-1-phenylpropan-1-one of Example 33, corresponding raw materials were subjected to the operations according to Example 33→Example 34→Example 35 to give the following compounds.

Example 37 (1)

4-(4-Benzoyl-1,3-thiazol-2-yl)-N-[4-(trifluoromethyl)phenyl]-1-piperidinecarboxamide TLC: Rf 0.40 (hexane:acetate=1:1);
$^1$H-NMR (CDCl$_3$): δ 8.17-8.13 (m, 2H), 8.11 (s, 1H), 7.64-7.47 (m, 7H), 6.66 (brs, 1H), 4.27-4.16 (m, 2H), 3.35 (tt, J=11.7, 3.6 Hz, 1H), 3.13 (dt, J=11.7, 2.7 Hz, 2H), 2.33-2.23 (m, 2H), 1.92 (dq, J=11.7, 3.6 Hz, 2H).

Example 37 (2)

4-{4-[(E)-2-phenylvinyl]-1,3-thiazol-2-yl}-N-[4-(trifluoromethyl)phenyl]-1-piperidinecarboxamide TLC: Rf 0.40 (hexane:acetate=2:1);
$^1$H-NMR (CDCl$_3$): δ 7.56-7.47 (m, 6H), 7.44 (d, J=15.9 Hz, 1H), 7.38-7.33 (m, 2H), 7.26 (tt, J=7.5, 1.2 Hz, 1H), 7.071 (s, 1H), 7.068 (d, J=15.9 Hz, 1H), 6.59 (brs, 1H), 4.22-4.17 (m, 2H), 3.30 (tt, J=11.4, 3.9 Hz, 1H), 3.14 (dt, J=11.4, 3.0 Hz, 2H), 2.29-2.23 (m, 2H), 1.91 (dq, J=11.4, 3.9 Hz, 2H).

Example 37 (3)

4-(5-Isopropyl-4-phenyl-1,3-thiazol-2-yl)-N-[4-(trifluoromethyl)phenyl]-1-piperidinecarboxamide TLC: Rf 0.63 (acetate);
$^1$H-NMR (CDCl$_3$): δ 7.58-7.31 (m, 9H), 6.55 (s, 1H), 4.24-4.14 (m, 2H), 3.50-3.38 (m, 1H), 3.30-3.18 (m, 1H), 3.17-3.05 (m, 2H), 2.28-2.18 (m, 2H), 1.97-1.81 (m, 2H), 1.32 (d, J=6.9 Hz, 6H).

Example 37 (4)

4-(4-Phenyl-1,3-thiazol-2-yl)-N-[4-(trifluoromethyl)phenyl]-1-piperidinecarboxamide TLC: Rf 0.47 (hexane:acetate=1:1);
$^1$H-NMR (CDCl$_3$): δ 7.88 (d, J=7.5 Hz, 2H), 7.55 (d, J=7.5 Hz, 2H), 7.48 (d, J=7.5 Hz, 2H), 7.45-7.29 (m, 4H), 6.56 (s, 1H), 4.25-4.13 (m, 2H), 3.37-3.25 (m, 1H), 3.23-3.08 (m, 2H), 2.46-2.20 (m, 2H), 2.03-1.85 (m, 2H).

Example 37 (5)

4-[4-(4-Pyridyl)-1,3-thiazol-2-yl]-N-[4-(trifluoromethyl)phenyl]-1-piperidinecarboxamide $^1$H-NMR (CDCl$_3$): δ 8.67-8.62 (m, 2H), 7.80-7.69 (m, 2H), 7.62 (s, 1H), 7.58-7.45 (m, 4H), 6.68 (s, 1H), 4.27-4.15 (m, 2H), 3.37-3.27 (m, 1H), 3.21-3.10 (m, 2H), 2.27 (dd, J=13.1, 2.7 Hz, 2H), 1.99-1.86 (m, 2H).

Example 37 (6)

4-[4-(2-Pyridyl)-1,3-thiazol-2-yl]-N-[4-(trifluoromethyl)phenyl]-1-piperidinecarboxamide $^1$H-NMR (DMSO-d$_6$): δ 8.94 (s, 1H), 8.61-8.57 (m, 1H), 8.17-8.14 (m, 1H), 8.04 (d, J=7.9 Hz, 1H), 7.86 (td, J=7.7, 1.9 Hz, 1H), 7.69 (d, J=8.6 Hz, 2H), 7.57 (d, J=8.8 Hz, 2H), 7.33 (ddd, J=7.5, 4.8, 1.2 Hz, 1H), 4.23 (d, J=13.5 Hz, 2H), 3.40-3.28 (m, 1H), 3.03 (t, J=11.7 Hz, 2H), 2.14 (d, J=10.1 Hz, 2H), 1.71 (td, J=12.1, 8.7 Hz, 2H).

Example 38

3-[2-(4-Piperidinyl-1,3-thiazol-4-yl]pyridine dihydrobromide

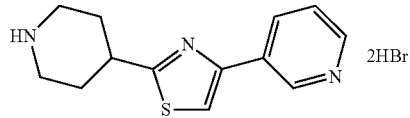

[Chemical Formula 40]

3-(Bromoacetyl)pyridine hydrobromide (12 g) was dissolved in methanol (129 mL) and water (14 mL) to give Liquid A, while tert-butyl 4-(aminocarbothioyl)tetrahydropyridine-1 (2H)-carboxylate (10 g) was dissolved in methanol (141 mL) to give Liquid B, and they were subjected to flow synthesis using a flow reactor (FlowSyn) manufactured by Uniqsis. As a coil reactor, a stainless steel coil reactor (20 mL) manufactured by Uniqsis was used. Under conditions set at a reaction temperature of 130° C. and a holding time of 5 minutes, the rector was continuously operated for about 1 hour (Liquid A: 2.0 mL/min, Liquid B: 2.0 mL/min). The resulting reaction liquid was concentrated under reduced pressure to give the title compound (14.2 g) having the following physical properties.

TLC: Rf 0.20 (methanol:28% aqueous ammonia solution=20:1);
$^1$H-NMR (DMSO-d$_6$): δ 9.37 (d, J=1.8 Hz, 1H), 8.95 (dt, J=1.8, 8.1 Hz, 1H), 8.86 (d, J=5.4 Hz, 1H), 8.80 (bs, 1H), 8.60 (bs, 1H), 8.56 (s, 1H), 8.66 (dd, J=5.4, 8.1 Hz, 1H), 3.49

(tt, J=3.9, 11.4 Hz, 1H), 3.45-3.30 (m, 2H), 3.20-3.00 (m, 2H), 2.34-2.18 (m, 2H), 2.08-1.86 (m, 2H).

Example 39

3-[2-(4-Piperidinyl-1,3-thiazol-4-yl]pyridine

[Chemical Formula 41]

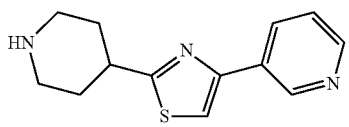

A 2N aqueous sodium hydroxide solution (100 mL) and purified water (100 mL) were added to the compound produced in Example 38 (14.2 g), followed by extraction twice with methylene chloride (200 mL). The organic layer was washed with purified water (100 mL) and saturated saline (100 mL), then dried using anhydrous sodium sulfate, and concentrated under reduced pressure. The resulting residue was purified by basic silica gel column chromatography (hexane:ethyl acetate=3:7) to give the title compound (6.85 g) having the following physical properties.
TLC: Rf 0.20 (methanol:28% aqueous ammonia solution=20:1);
$^1$H-NMR (DMSO-$d_6$): δ 9.14 (d, J=2.4 Hz, 1H), 8.52 (dd, J=1.2, 4.5 Hz, 1H), 8.30-8.22 (m, 1H), 8.14 (s, 1H), 7.45 (dd, J=4.5 Hz, 8.1 Hz, 1H), 3.11 (tt, J=3.9, 12.3 Hz, 1H), 3.00 (dt, J=3.9, 12.3 Hz, 2H), 2.66-2.53 (m, 2H), 2.04-1.91 (m, 2H), 1.58 (dq, J=3.9, 12.3 Hz, 2H).

Example 40

4-[4-(3-Pyridyl)-1,3-thiazol-2-yl]-N-[4-(trifluoromethyl)phenyl]-1-piperidinecarboxamide

[Chemical Formula 42]

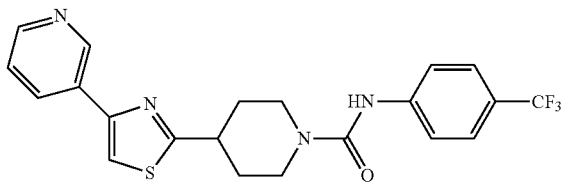

The compound produced in Example 39 was subjected to the operations according to Example 10 to give the title compound having the following physical properties.
TLC: Rf 0.57 (ethyl acetate);
$^1$H-NMR (DMSO-$d_6$): δ 9.14 (dd, J=2.3, 0.8 Hz, 1H), 8.94 (s, 1H), 8.52 (dd, J=4.8, 2.3 Hz, 1H), 8.30-8.25 (m, 1H), 8.18 (s, 1H), 7.71-7.63 (m, 2H), 7.60-7.54 (m, 2H), 7.45 (ddd, J=8.0, 4.8, 0.8 Hz, 1H), 4.23 (m, 2H), 3.40-3.33 (m, 1H), 3.03 (m, 2H), 2.14 (m, 2H), 1.70 (m, 2H).

Example 41

4-(4-Phenyl-1,3-thiazol-2-yl)-N-[5-(trifluoromethyl)-2-pyridyl]-1-piperidinecarboxamide In place of 2-bromo-1-phenylpropan-1-one of Example 33, 2-bromo-1-phenylethan-1-one was subjected to the operations according to Example 33→Example 34→Example 4 to give the title compound having the following physical properties.
TLC: Rf 0.74 (hexane:acetate=2:1);
$^1$H-NMR (CDCl$_3$): δ 8.45 (d, J=0.9 Hz, 1H), 8.18 (d, J=8.7 Hz, 1H), 3.93-7.81 (m, 3H), 7.48-7.28 (m, 5H), 4.28-4.17 (m, 2H), 3.34 (tt, J=3.9, 10.8 Hz, 1H), 3.25-3.11 (m, 2H), 2.35-2.22 (m, 2H), 2.03-1.85 (m, 2H).

Example 42

4-(4-Phenyl-1,3-thiazol-2-yl)-N-[6-(trifluoromethyl)-3-pyridyl]-1-piperidinecarboxamide In place of 2-bromo-1-phenylpropan-1-one of Example 33, 2-bromo-1-phenylethan-1-one was subjected to the operations according to Example 33→Example 34→Example 5 to give the title compound having the following physical properties.
TLC: Rf 0.31 (hexane:acetate=1:1);
$^1$H-NMR (CDCl$_3$): δ 8.49 (d, J=2.4 Hz, 1H), 8.24 (dd, J=8.4, 2.4 Hz, 1H), 7.87 (d, J=7.2 Hz, 2H), 7.62 (d, J=8.4 Hz, 1H), 7.45-7.28 (m, 4H), 6.66 (s, 1H), 4.25-4.15 (m, 2H), 3.34 (m, 1H), 3.26-3.15 (m, 2H), 2.35-2.24 (m, 2H), 2.04-1.88 (m, 2H).

Example 43

4-{4-[Hydroxy(phenyl)methyl]-1,3-thiazol-2-yl}-N-[4-(trifluoromethyl)phenyl]-1-piperidinecarboxamide The compound produced in Example 37 (1) (315 mg) was dissolved in methanol (3 mL), and sodium borohydride (25.9 mg) was added and the mixture was stirred at room temperature for 20 minutes. An aqueous saturated ammonium chloride solution was added to the reaction solution, and the solvent was distilled off under reduced pressure, followed by extraction with ethyl acetate. The organic layer was washed with saturated saline, dried over anhydrous sodium sulfate, then concentrated to give the title compound (316 mg) having the following physical properties.
TLC: Rf 0.50 (hexane:acetate=1:2);
$^1$H-NMR (CDCl$_3$): δ 7.53 (d, J=8.7 Hz, 2H), 7.46 (d, J=8.7 Hz, 2H), 7.44-7.30 (m, 5H), 6.84 (d, J=0.9 Hz, 1H), 6.61 (brs, 1H), 5.89 (brs, 1H), 4.20-4.11 (m, 2H), 3.27-3.17 (m, 2H), 3.07 (dt, J=12.0, 2.7 Hz, 2H), 2.24-2.13 (m, 2H), 1.84 (dq, J=12.0, 4.2 Hz, 2H).

Example 44

4-(4-Benzyl-1,3-thiazol-2-yl)-N-[4-(trifluoromethyl)phenyl]-1-piperidinecarboxamide The compound produced in Example 43 (20 mg) was dissolved in methylene chloride (3 mL), and triethylsilane (0.035 mL) and trifluoroacetic acid (0.03 mL) were added and the mixture was heated under reflux for 24 hours. The reaction solution was cooled to room temperature, and then an aqueous saturated sodium hydrogen carbonate solution was added, followed by extraction with methylene chloride. The organic layer was washed with saturated saline, dried over anhydrous sodium sulfate, and then concentrated. The resulting residue was purified by silica gel column chromatography (hexane:ethyl acetate=1:1 to 1:4) to give the title compound (14 mg) having the following physical properties.

TLC: Rf 0.70 (hexane:acetate=1:2);
$^1$H-NMR (CDCl$_3$): δ 7.53 (d, J=9.0 Hz, 2H), 7.47 (d, J=9.0 Hz, 2H), 7.34-7.20 (m, 5H), 6.65 (t, J=0.9 Hz, 1H), 6.59 (brs, 1H), 4.19-4.15 (m, 2H), 4.10 (brs, 2H), 3.23 (tt, J=11.4, 3.9 Hz, 1H), 3.08 (dt, J=11.4, 3.0 Hz, 2H), 2.23-2.16 (m, 2H), 1.84 (dq, J=11.4, 3.9 Hz, 2H).

Example 45

4-{4-[Ethoxy(phenyl)methyl]-1,3-thiazol-2-yl}-N-[4-(trifluoromethyl)phenyl]-1-piperidinecarboxamide A mixture (100 mg) of the compound produced in Example 43 and ethanol was dissolved in methylene chloride (3 mL), and triethylsilane (0.069 mL) and trifluoroacetic acid (0.081 mL) were added and the mixture was heated under reflux for 21 hours. The reaction solution was cooled to room temperature, and then an aqueous saturated sodium hydrogen carbonate solution was added, followed by extraction with methylene chloride. The organic layer was washed with saturated saline, dried over anhydrous sodium sulfate, and then concentrated. The resulting residue was purified by silica gel column chromatography (hexane:ethyl acetate=3:1 to 1:4) to give the title compound (45 mg) having the following physical properties.

TLC: Rf 0.70 (hexane:acetate=1:2);
$^1$H-NMR (CDCl$_3$): δ 7.53 (d, J=8.7 Hz, 2H), 7.46 (d, J=8.7 Hz, 2H), 7.44-7.27 (m, 5H), 7.00 (s, 1H), 6.54 (brs, 1H), 5.53 (s, 1H), 4.20-4.08 (m, 2H), 3.65-3.50 (m, 2H), 3.24 (tt, J=11.4, 3.6 Hz, 1H), 3.12-3.00 (m, 2H), 2.23-2.12 (m, 2H), 1.89-1.73 (m, 2H), 1.27 (t, J=6.9 Hz, 3H).

Example 46

4-[4-(2-Phenylethyl-1,3-thiazol-2-yl]-N-[4-(trifluoromethyl)phenyl]-1-piperidinecarboxamide The compound produced in Example 37 (2) (100 mg) was dissolved in ethanol (3 mL), and 10% palladium/carbon (10 mg) was added and the mixture was stirred in a hydrogen atmosphere at room temperature for 3.5 hours. In an argon atmosphere, 10% palladium/carbon (20 mg) was further added and the resulting mixture was stirred in a hydrogen atmosphere at room temperature for 1 hour, and then the catalyst was removed by filtration using Celite. The filtrate was concentrated under reduced pressure to give the title compound (95 mg) having the following physical properties.

TLC: Rf 0.60 (hexane:acetate=1:1);
$^1$H-NMR (CDCl$_3$): δ 7.54 (d, J=9.0 Hz, 2H), 7.48 (d, J=9.0 Hz, 2H), 7.30-7.16 (m, 5H), 6.73 (s, 1H), 6.57 (brs, 1H), 4.23-4.14 (m, 2H), 3.25 (tt, J=11.4, 3.9 Hz, 1H), 3.16-2.98 (m, 6H), 2.27-2.17 (m, 2H), 1.86 (dq, J=11.4, 3.9 Hz, 2H).

Example 47

4-Methyl-4-(5-methyl-4-phenyl-1,3-thiazol-2-yl)-N-[4-(trifluoromethyl)phenyl]-1-piperidinecarboxamide In place of tert-butyl 4-carbamothioylpiperidine-1-carboxylate of Example 33, 1,1-dimethylethyl 4-(aminothioxomethyl)-4-methyl-1-piperidinecarboxylate was subjected to the operations according to Example 33→Example 34→Example 35 to give the title compound having the following physical properties.

TLC: Rf 0.33 (hexane:acetate=3:1);
$^1$H-NMR (CDCl$_3$): δ 7.68-7.60 (m, 2H), 7.53-7.28 (m, 7H), 6.60 (s, 1H), 3.79 (dt, J=13.5, 3.5 Hz, 2H), 3.42 (ddd, J=13.5, 10.3, 3.5 Hz, 2H), 2.55 (s, 3H), 2.34 (dt, J=13.5, 3.5 Hz, 2H), 1.79 (ddd, J=13.5, 10.3, 3.5 Hz, 2H), 1.42 (s, 3H).

Example 48

Benzyl-[4-(5-methyl-4-phenyl-1,3-thiazol-2-yl)-1-{[4-(trifluoromethyl)phenyl]carbamoyl}-4-piperidinyl]carbamate

[Chemical Formula 43]

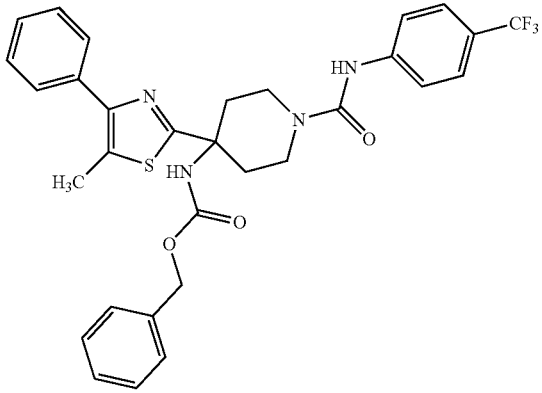

In place of tert-butyl 4-carbamothioylpiperidine-1-carboxylate of Example 33, tert-butyl 4-(benzyloxycarbonylamino)-4-carbamothioyl-piperidine-1-carboxylate was subjected to the operations according to Example 33→Example 34→Example 35 to give the title compound having the following physical properties.

TLC: Rf 0.46 (hexane:ethyl acetate=3:2);
$^1$H-NMR (CDCl$_3$): δ 7.62-7.55 (m, 2H), 7.51 (d, J=8.7 Hz, 2H), 7.48-7.35 (m, 4H), 7.35-7.25 (m, 5H), 6.60 (s, 1H), 5.32 (s, 1H), 5.09 (s, 2H), 3.87 (dt, J=4.2, 13.8 Hz, 2H), 3.48-3.31 (m, 2H), 2.52 (s, 3H), 2.50-2.32 (m, 4H).

Example 49

4-Amino-4-(5-methyl-4-phenyl-1,3-thiazol-2-yl)-N-[4-(trifluoromethyl)phenyl]-1-piperidinecarboxamide The compound produced in Example 48 (252 mg) was dissolved in methanol (3 mL), and 10% palladium/carbon (water content: 50%, 150 mg) was added. The mixture was stirred in a hydrogen atmosphere at room temperature for 24 hours. After the catalyst was filtered, the filtrate was concentrated under reduced pressure. The resulting residue was purified by silica gel column chromatography (hexane:ethyl acetate=3:7) to give the title compound (156 mg) having the following physical properties.

TLC: Rf 0.66 (hexane:acetate=1:4);
$^1$H-NMR (DMSO-d$_6$): δ 9.08 (s, 1H), 7.75-7.63 (m, 4H), 7.57 (d, J=8.4 Hz, 2H), 7.48 (t, J=7.5 Hz, 2H), 7.43-7.33 (m, 1H), 4.05-3.85 (m, 2H), 3.40-3.20 (m, 2H), 2.60 (s, 3H), 2.46-2.33 (m, 2H), 2.18-2.02 (m, 2H).

Example 50

4-Acetamido-4-(5-methyl-4-phenyl-1,3-thiazol-2-yl)-N-[4-(trifluoromethyl)phenyl]-1-piperidinecarboxamide The compound produced in Example 49 (32 mg) was dissolved in dimethylformamide (1 mL), and acetic anhydride (70 mg) and dimethylaminopyridine (17 mg) were added and the mixture was stirred at room temperature overnight. Water (5 mL) was added to the reaction solution, followed by extraction twice with ethyl acetate (10 mL). The organic layer was washed with saturated saline (20 mL), then dried over anhydrous sodium sulfate, and concentrated under reduced pressure. The resulting residue was purified by silica gel column chromatography (methylene chloride: tert-butyl methyl ether=1:1) to give the title compound (25 mg) having the following physical properties.

TLC: Rf 0.46 (hexane:acetate=1:4);

$^1$H-NMR (DMSO-d$_6$): δ 8.91 (s, 1H), 8.41 (s, 1H), 7.71-7.60 (m, 4H), 7.56 (d, J=8.7 Hz, 2H), 7.43 (t, J=6.9 Hz, 2H), 7.34-7.27 (m, 1H), 4.05-3.91 (m, 2H), 3.25-3.10 (m, 2H), 2.60-2.33 (m, 5H), 2.13-1.98 (m, 2H), 1.94 (s, 3H).

Example 51

4-(5-Methyl-4-phenyl-1,3-thiazol-2-yl)-4-[(methyl-sulfonyl)amino]-N-[4-(trifluoromethyl)phenyl]-1-piperidinecarboxamide

[Chemical Formula 44]

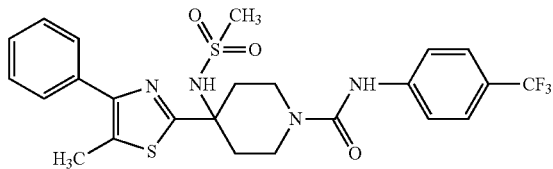

The compound produced in Example 49 (70 mg) was dissolved in methylene chloride (2 mL), and triethylamine (61 mg) and methanesulfonyl chloride (69 mg) were added and the mixture was stirred at room temperature for 2 hours. The reaction solution was concentrated under reduced pressure, and the resulting residue was purified by silica gel column chromatography (hexane:ethyl acetate=1:1) to give the title compound (28 mg) having the following physical properties.

TLC: Rf 0.40 (hexane:acetate=1:1);

$^1$H-NMR (CDCl$_3$): δ 7.61 (d, J=8.4 Hz, 2H), 7.52 (d, J=8.4 Hz, 2H), 7.46 (d, J=8.4 Hz, 2H), 7.46-7.32 (m, 3H), 6.63 (s, 1H), 5.10 (s, 1H), 3.83 (dt, J=9.0, 4.2 Hz, 2H), 3.67 (ddd, J=10.5, 10.2, 3.3 Hz, 2H), 2.63 (s, 3H), 2.59 (s, 3H), 2.55-2.42 (m, 2H), 2.29 (ddd, J=10.5, 10.2, 3.3 Hz, 2H).

Example 52

2-Methyl-2-propanil

4-[5-(ethoxycarbonyl)-4-phenyl-1,3-thiazol-2-yl]-1-piperidinecarboxylate

[Chemical Formula 45]

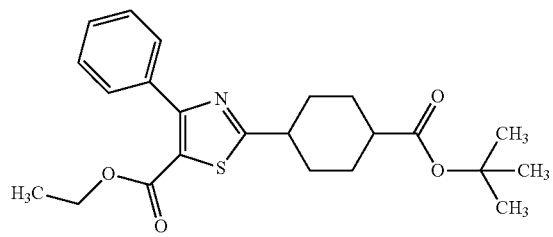

In place of 2-bromo-1-phenylpropan-1-one of Example 33, ethyl 2-bromo-3-oxo-3-phenylpropanoate was subjected to the operations according to Example 33 to give the title compound having the following physical properties.

TLC: Rf 0.60 (hexane:acetate=7:3);

Example 53

Ethyl 4-phenyl-2-(4-piperidinyl)-1,3-thiazole-5-carboxylate

[Chemical Formula 46]

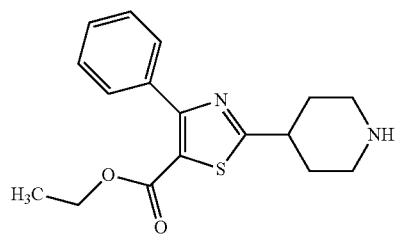

Trifluoroacetic acid (15 mL) was added to a solution (30 mL) of the compound produced in Example 52 in methylene chloride and the mixture was stirred overnight. After the mixture was concentrated under reduced pressure and subjected to azeotropy with toluene, the residue was purified by silica gel column chromatography (ethyl acetate:methanol=9:1) to give the title compound having the following physical properties.

TLC: Rf 0.34 (ethyl acetate);

$^1$H-NMR (CDCl$_3$): δ 7.68-7.75 (m, 2H), 7.45-7.38 (m, 3H), 4.25 (q, J=7.2 Hz, 2H), 3.25-3.08 (m, 3H), 2.82-2.70 (m, 2H), 2.20-2.10 (m, 2H), 1.82-1.65 (m, 2H), 1.27 (t, J=7.2 Hz, 3H).

Example 54

4-(5-Acetyl-4-phenyl-1,3-thiazol-2-yl)-N-[4-(trifluoromethyl)phenyl]-1-piperidinecarboxamide The compound produced in Example 53 (600 mg) was dissolved in tetrahydrofuran (3 mL), and a lanthanum chloride (III) lithium chloride complex tetrahydrofuran solution (0.66M, 0.58 mL) and a methylmagnesium bromide tetrahydrofuran solution (0.99M, 6.65 mL) were successively added dropwise under ice-cooling. After the mixture was stirred at room temperature for 1 hour, 1N hydrochloric acid was added thereto and the resulting mixture was filtered through Celite. The filtrate was concentrated under reduced pressure, and the resulting residue was purified by silica gel column chromatography to give an intermediate amine (54 mg). The obtained intermediate amine was subjected to the operations according to Example 10 to give the title compound having the following physical properties.

TLC: Rf 0.45 (hexane:ethyl acetate, 1:1);

$^1$H-NMR (CDCl$_3$): δ 7.60-7.42 (m, 9H), 6.54 (s, 1H), 4.25-4.15 (m, 2H), 3.32-3.20 (m, 1H), 3.16-3.04 (m, 2H), 2.30-2.20 (m, 2H), 2.19 (s, 3H), 2.00-1.80 (m, 2H).

Example 55

4-[5-(1-Hydroxyethyl-4-phenyl-1,3-thiazol-2-yl]-N-[4-(trifluoromethyl)phenyl]-1-piperidinecarboxamide The compound produced in Example 54 (18 mg) was dissolved in methanol (2 mL), and sodium borohydride (1.87 g) was added under ice-cooling. After the mixture was stirred at room temperature for 2 hours, water was added, followed by concentration under reduced pressure. The resulting residue was purified by silica gel column chromatography (hexane:ethyl acetate=9:1 to ethyl acetate) to give the title compound (15 mg) having the following physical properties.

TLC: Rf 0.40 (hexane:acetate=1:1);
$^1$H-NMR (CDCl$_3$): δ 7.64-7.34 (m, 9H), 6.56 (s, 1H), 5.34-5.24 (m, 1H), 4.24-4.10 (m, 2H), 3.32-3.20 (m, 1H), 3.19-3.04 (m, 2H), 2.30-2.18 (m, 2H), 2.10-2.06 (m, 1H), 2.00-1.80 (m, 2H) 1.62 (d, J=6.3 Hz, 3H).

Example 56

Ethyl 4-phenyl-2-(1-{[4-(trifluoromethyl)phenyl]carbamoyl}-4-piperidinyl)-1,3-thiazole-5-carboxylate The compound produced in Example 53 was subjected to the operations according to Example 10 to give the title compound having the following physical properties.

TLC: Rf 0.22 (hexane:ethyl acetate=1:1);
$^1$H-NMR (CDCl$_3$): δ 7.76-7.68 (m, 2H), 7.54 (d, J=9.0 Hz, 2H), 7.47 (d, J=9.0 Hz, 2H), 7.45-7.38 (m, 3H), 6.53 (s, 1H), 4.26 (q, J=7.2 Hz, 2H), 4.25-4.15 (m, 2H), 3.35-3.20 (m, 1H), 3.20-3.05 (m, 2H), 2.33-2.20 (m, 2H), 2.00-1.83 (m, 2H), 1.28 (t, J=7.2 Hz, 3H).

Example 57

4-[5-(Hydroxymethyl)-4-phenyl-1,3-thiazol-2-yl]-N-[4-(trifluoromethyl)phenyl]-1-piperidinecarboxamide The compound produced in Example 56 was subjected to the operations according to Example 12 to give the title compound having the following physical properties.

TLC: Rf 0.61 (hexane:acetate=1:1);
$^1$H-NMR (CDCl$_3$): δ 7.66-7.60 (m, 2H), 7.56-7.34 (m, 7H), 6.55 (s, 1H), 4.91 (d, J=5.4 Hz, 2H), 4.25-4.10 (m, 2H), 3.32-3.20 (m, 1H), 3.19-3.04 (m, 2H), 2.30-2.18 (m, 2H), 2.10-2.00 (m, 1H), 2.00-1.80 (m, 2H).

Example 58

4-Phenyl-2-(1-{[4-(trifluoromethyl)phenyl]carbamoyl}-4-piperidinyl)-1,3-thiazole-5-carboxylic acid The compound produced in Example 56 (130 mg) was dissolved in methanol (3 mL) and tetrahydrofuran (2 mL), and a 2N aqueous sodium hydroxide solution (2 mL) was added. After the mixture was stirred overnight, 2N hydrochloric acid was added thereto to make it weakly acidic, followed by extraction with ethyl acetate. The organic layer was dried, and then the solvent was distilled off under reduced pressure to give the title compound (122 mg) having the following physical properties.

TLC: Rf 0.28 (methylene chloride:ethyl acetate:methanol=8:4:1);
$^1$H-NMR (CDCl$_3$): δ 7.77-7.70 (m, 2H), 7.54 (d, J=8.7 Hz, 2H), 7.50-7.39 (m, 5H), 6.57 (s, 1H), 4.25-4.15 (m, 2H), 3.35-3.23 (m, 1H), 3.19-3.06 (m, 2H), 2.33-2.20 (m, 2H), 2.20-1.70 (m, 3H).

Example 59

4-(5-Carbamoyl-4-phenyl-1,3-thiazol-2-yl)-N-[4-(trifluoromethyl)phenyl]-1-piperidinecarboxamide The compound produced in Example 58 (270 mg) was dissolved in N,N-dimethylformamide (5 mL), and 1-hydroxybenzotriazole monohydrate (85 mg), 1-ethyl-3-(3-dimethylaminopropyl)carbodiimide hydrochloride (122 mg), and ammonium chloride (308 mg) were added and the mixture was stirred overnight. Purification was performed by silica gel column chromatography (ethyl acetate:methanol=9:1) to give the title compound (41 mg) having the following physical properties.

TLC: Rf 0.54 (methylene chloride:ethyl acetate:methanol=8:4:1);
$^1$H-NMR (CDCl$_3$): δ 7.66-7.60 (m, 2H), 7.57-7.44 (m, 7H), 6.58 (s, 1H), 5.80-5.50 (br, 2H), 4.24-4.14 (m, 2H), 3.32-3.20 (m, 1H), 3.17-3.04 (m, 2H), 2.30-2.20 (m, 2H), 2.00-1.82 (m, 2H).

Example 60

4-(5-Cyano-4-phenyl-1,3-thiazol-2-yl)-N-[4-(trifluoromethyl)phenyl]-1-piperidinecarboxamide

[Chemical Formula 47]

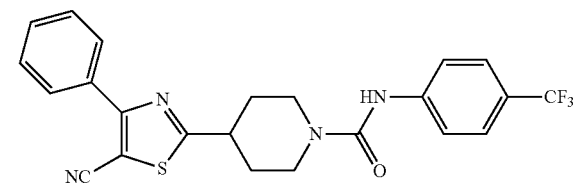

The compound produced in Example 59 (100 mg) was dissolved in methylene chloride (5 mL), and pyridine (0.3 mL) and trifluoroacetic anhydride (0.17 mL) were added and the mixture was stirred at 50° C. overnight. The organic layer was washed with water, then the organic layer was dried, and the solvent was distilled off under reduced pressure. The resulting residue was purified by silica gel column chromatography (hexane:ethyl acetate=9:1 to ethyl acetate) to give the title compound (41 mg) having the following physical properties.

TLC: Rf 0.44 (hexane:acetate=1:1);
$^1$H-NMR (CDCl$_3$): δ 8.15-8.08 (m, 2H), 7.58-7.45 (m, 7H), 6.55 (s, 1H), 4.28-4.15 (m, 2H), 3.38-3.26 (m, 1H), 3.22-3.08 (m, 2H), 2.34-2.22 (m, 2H), 2.02-1.84 (m, 2H).

Example 61

2-Methyl-2-propanil 4-[4-(phenylcarbamoyl)-1,3-thiazol-2-yl]-1-piperidinecarboxylate

[Chemical Formula 48]

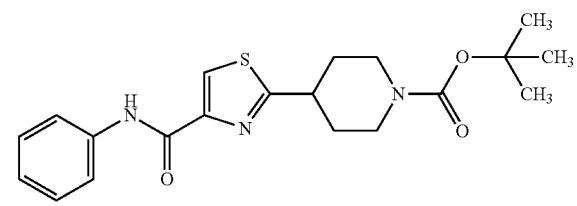

2-(1-tert-Butoxycarbonyl-4-pyridyl)thiazole-4-carboxylic acid (70 mg) and aniline (41 mg) were dissolved in tetrahydrofuran (2 mL), and 4-(4,6-dimethoxy-1,3,5-triazin-2-yl)-4-methyl-morpholinium-chloride (124 mg) was added and the mixture was stirred at room temperature overnight. 1N hydrochloric acid and ethyl acetate were added to the reaction solution, followed by extraction. The organic layer was washed with an aqueous saturated sodium hydrogen carbonate solution and saturated saline and dried over sodium sulfate. The solvent was distilled off under reduced pressure, and then the resulting residue was purified by silica gel chromatography to give the title compound (100 mg) having the following physical properties.

TLC: Rf 0.52 (hexane:acetate=2:1);

$^1$H-NMR (CDCl$_3$): δ 9.20 (brs, 1H), 8.10 (s, 1H), 7.75-7.70 (m, 2H), 7.40-7.30 (m, 2H), 7.20-7.10 (m, 1H), 4.30-4.20 (m, 2H), 3.20-3.10 (m, 1H), 3.00-2.85 (m, 2H), 2.20-2.10 (m, 2H), 1.90-1.70 (m, 2H), 1.48 (s, 9H).

Example 62

N-phenyl-2-(4-piperidinyl)-1,3-thiazole-4-carboxamide

[Chemical Formula 49]

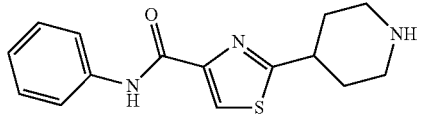

The compound produced in Example 61 (100 mg) was dissolved in a 4N hydrogen chloride/1,4-dioxane solution (5 mL) and the mixture was stirred at room temperature overnight. The reaction solution was distilled off under reduced pressure, and then 1N hydrochloric acid (20 mL) and tert-butyl methyl ether were added to cause separation. A 1N aqueous sodium hydroxide solution was added to the tank to make it basic, followed by extraction with tert-butyl methyl ether. The organic layer was washed with saturated chloride saturated saline and then dried using anhydrous sodium sulfate. The solvent was distilled off under reduced pressure to give the title compound (57 mg) having the following physical properties.

$^1$H-NMR (CDCl$_3$): δ 9.20 (brs, 1H), 8.08 (s, 1H), 7.72-7.65 (m, 2H), 7.40-7.30 (m, 2H), 7.20-7.10 (m, 1H), 3.30-3.10 (m, 3H), 3.85-2.70 (m, 2H), 2.20-2.10 (m, 2H), 1.90-1.70 (m, 2H).

Example 63

4-[4-(Phenylcarbamoyl)-1,3-thiazol-2-yl]-N-[4-(trifluoromethyl)phenyl]-1-piperidinecarboxamide The compound produced in Example 62 was subjected to the operations according to Example 10 to give the title compound having the following physical properties.

TLC: Rf 0.61 (hexane:acetate=1:2);

$^1$H-NMR (CDCl$_3$): δ 9.20 (brs, 1H), 8.12 (s, 1H), 7.75-7.70 (m, 2H), 7.60-7.40 (m, 4H), 7.40-7.30 (m, 2H), 7.20-7.10 (m, 1H), 6.55 (brs, 1H), 4.30-4.20 (m, 2H), 3.40-3.20 (m, 1H), 3.20-3.05 (m, 2H), 2.30-2.20 (m, 2H), 2.00-1.80 (m, 2H).

Example 64

2-Methyl-2-propanil

4-{4-[methyl(phenyl)carbamoyl]-1,3-thiazol-2-yl}-1-piperidinecarboxylate

[Chemical Formula 50]

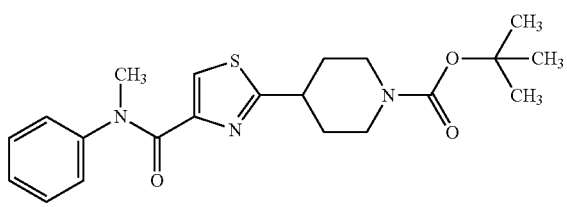

In place of aniline of Example 61, N-methylaniline was subjected to the operations according to Example 61 to give the title compound having the following physical properties.

TLC: Rf 0.52 (hexane:acetate=2:1);

$^1$H-NMR (CDCl$_3$): δ 7.50 (s, 1H), 7.30-7.15 (m, 3H), 7.20-7.10 (m, 2H), 4.00-3.85 (m, 2H), 3.49 (s, 3H), 3.00-2.75 (m, 3H), 1.90-1.75 (m, 2H), 1.50-1.40 (m, 2H), 1.47 (s, 9H).

Example 65

N-methyl-N-phenyl-2-(4-piperidinyl)-1,3-thiazole-4-carboxamide

[Chemical Formula 51]

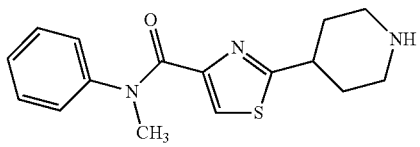

The compound produced in Example 64 was subjected to the operations according to Example 62 to give the title compound having the following physical properties.

$^1$H-NMR (CDCl$_3$): δ 7.42 (s, 1H), 7.30-7.15 (m, 3H), 7.15-7.05 (m, 2H), 3.49 (s, 3H), 3.10-3.00 (m, 2H), 3.00-2.80 (m, 1H), 2.70-2.60 (m, 2H), 1.90-1.80 (m, 2H), 1.60-1.40 (m, 2H).

Example 66

4-{4-[Methyl(phenyl)carbamoyl]-1,3-thiazol-2-yl}-N-[4-(trifluoromethyl)phenyl]-1-piperidinecarboxamide The compound produced in Example 65 was subjected to the operations according to Example 10 to give the title compound having the following physical properties.

TLC: Rf 0.24 (hexane:acetate=1:2);

$^1$H-NMR (CDCl$_3$): δ 7.60-7.50 (m, 6H), 7.30-7.15 (m, 2H), 7.15-7.10 (m, 2H), 6.55 (brs, 1H), 4.00-3.85 (m, 2H), 3.49 (2, 3H), 3.15-3.00 (m, 3H), 2.00-1.80 (m, 2H), 1.60-1.50 (m, 2H).

Examples 67 (1) to 67 (7)

In place of ethyl 2-bromo-3-oxo-3-phenylpropanoate of Example 52, corresponding compounds were subjected to the operations according to Example 52→Example 53→Example 10 to give the following compounds.

Example 67 (1)

Ethyl 4-(2-thienyl)-2-(1-{[4-(trifluoromethyl)phenyl]carbamoyl}-4-piperidinyl)-1,3-thiazole-5-carboxylate TLC: Rf 0.60 (hexane:acetate=1:1);
$^1$H-NMR (CDCl$_3$): δ 8.35-8.31 (m, 1H), 7.60-7.42 (m, 5H), 7.14-7.08 (m, 1H), 6.54 (s, 1H), 4.35 (q, J=7.2 Hz, 2H), 4.25-4.10 (m, 2H), 3.30-3.20 (m, 3H), 2.30-2.20 (m, 2H), 2.00-1.80 (m, 2H), 1.38 (t, J=7.2 Hz, 3H).

Example 67 (2)

Ethyl 4-(2-fluorophenyl)-2-(1-{[4-(trifluoromethyl)phenyl]carbamoyl}-4-piperidinyl)-1,3-thiazole-5-carboxylate TLC: Rf 0.45 (hexane:acetate=1:1);
$^1$H-NMR (CDCl$_3$): δ 7.60-7.36 (m, 6H), 7.26-7.08 (m, 2H), 6.57 (s, 1H), 4.30-4.15 (m, 4H), 3.35-3.23 (m, 1H), 3.18-3.05 (m, 2H), 2.33-2.20 (m, 2H), 2.00-1.80 (m, 2H), 1.23 (t, J=7.2 Hz, 3H).

Example 67 (3)

Ethyl 4-(3-fluorophenyl)-2-(1-{[4-(trifluoromethyl)phenyl]carbamoyl}-4-piperidinyl)-1,3-thiazole-5-carboxylate

[Chemical Formula 52]

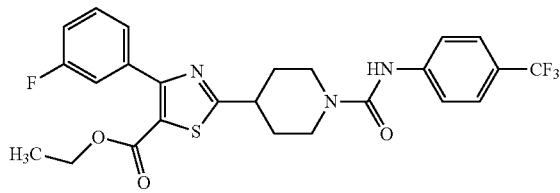

TLC: Rf 0.54 (hexane:acetate=1:1);
$^1$H-NMR (CDCl$_3$): δ 7.80-7.72 (m, 2H), 7.55 (d, J=9.0 Hz, 2H), 7.47 (d, J=9.0 Hz, 2H), 7.11 (t, 8.4 Hz, 2H), 6.54 (s, 1H), 4.27 (q, J=7.2 Hz, 2H), 4.25-4.15 (m, 2H), 3.33-3.20 (m, 1H), 3.20-3.05 (m, 2H), 2.32-2.20 (m, 2H), 2.00-1.80 (m, 2H), 1.30 (t, J=7.2 Hz, 3H).

Example 67 (4)

Ethyl 4-(4-fluorophenyl)-2-(1-{[4-(trifluoromethyl)phenyl]carbamoyl}-4-piperidinyl)-1,3-thiazole-5-carboxylate TLC: Rf 0.54 (hexane:acetate=1:1);
$^1$H-NMR (CDCl$_3$): δ 7.76 (dd, J=8.7, 5.4 Hz, 2H), 7.55 (d, 8.7 Hz, 2H), 7.47 (d, J=8.7 Hz, 2H), 7.11 (t, J=8.7 Hz, 2H), 6.52 (s, 1H), 4.28 (q, J=7.2 Hz, 2H), 4.25-4.15 (m, 2H), 3.35-3.20 (m, 1H), 3.20-3.07 (m, 2H), 2.30-2.20 (m, 2H), 2.00-1.82 (m, 2H), 1.30 (t, J=7.2 Hz, 3H).

Example 67 (5)

Ethyl 4-(4-phenoxyphenyl)-2-(1-{[4-(trifluoromethyl)phenyl]carbamoyl}-4-piperidinyl)-1,3-thiazole-5-carboxylate TLC: Rf 0.57 (hexane:acetate=1:1);
$^1$H-NMR (CDCl$_3$): δ 7.74 (d, J=8.7 Hz, 2H), 7.54 (d, J=8.7 Hz, 2H), 7.46 (d, J=8.7 Hz, 2H), 7.40-7.30 (m, 2H), 7.17-6.99 (m, 5H), 6.54 (s, 1H), 4.28 (q, J=7.2 Hz, 2H), 4.24-4.14 (m, 2H), 3.35-3.20 (m, 1H), 3.20-3.07 (m, 2H), 2.32-2.20 (m, 2H), 2.00-1.80 (m, 2H), 1.31 (t, J=7.2 Hz, 3H).

Example 67 (6)

Ethyl 4-(2-methyl-2-propanil)-2-(1-{[4-(trifluoromethyl)phenyl]carbamoyl}-4-piperidinyl)-1,3-thiazole-5-carboxylate TLC: Rf 0.67 (hexane:acetate=1:1);
$^1$H-NMR (CDCl$_3$): δ 7.53 (d, J=8.2 Hz, 2H), 7.47 (d, J=8.2 Hz, 2H), 6.56 (s, 1H), 4.30 (q, J=7.5 Hz, 2H), 4.18-4.08 (m, 2H), 3.20-3.06 (m, 3H), 2.25-2.13 (m, 2H), 1.93-1.75 (m, 2H), 1.48 (s, 9H), 1.36 (t, J=7.5 Hz, 3H).

Example 67 (7)

Methyl [4-phenyl-2-(1-{[4-(trifluoromethyl)phenyl]carbamoyl}-4-piperidinyl)-1,3-thiazol-5-yl]-acetate TLC: Rf 0.55 (hexane:acetate=1:1);
$^1$H-NMR (CDCl$_3$): δ 7.62-7.34 (m, 9H), 6.56 (s, 1H), 4.24-4.11 (m, 2H), 3.90 (s, 2H), 3.76 (s, 3H), 3.33-3.20 (m, 1H), 3.19-3.02 (m, 2H), 2.30-2.18 (m, 2H), 2.00-1.80 (m, 2H).

Examples 68 (1) to 68 (7)

The compounds obtained in Examples 67 (1) to 67 (7) were each subjected to the method according to Example 12 to give the following compounds.

Example 68 (1)

4-[5-(Hydroxymethyl)-4-(2-thienyl)-1,3-thiazol-2-yl]-N-[4-(trifluoromethyl)phenyl]-1-piperidinecarboxamide TLC: Rf 0.28 (hexane:acetate=1:1);
$^1$H-NMR (CDCl$_3$): δ 7.57-7.44 (m, 4H), 7.38-7.33 (m, 2H), 7.09 (dd, J=4.8, 3.9 Hz, 1H), 6.53 (s, 1H), 4.99 (d, J=5.7 Hz, 2H), 4.24-4.12 (m, 2H), 3.32-3.20 (m, 1H), 3.20-3.05 (m, 2H), 2.30-2.18 (m, 2H), 2.04 (t, J=5.7 Hz, 1H), 1.95-1.80 (m, 2H).

Example 68 (2)

4-[4-(2-Fluorophenyl-5-(hydroxymethyl)-1,3-thiazol-2-yl]-N-[4-(trifluoromethyl)phenyl]-1-piperidinecarboxamide TLC: Rf 0.19 (hexane:acetate=1:1);
$^1$H-NMR (CDCl$_3$): δ 7.60-7.44 (m, 5H), 7.43-7.34 (m, 1H), 7.28-7.12 (m, 2H), 6.53 (s, 1H), 4.75 (d, J=5.7 Hz, 2H), 4.24-4.14 (m, 2H), 3.34-3.22 (m, 1H), 3.18-3.06 (m, 2H), 2.30-2.20 (m, 2H), 2.07-1.82 (m, 3H).

Example 68 (3)

4-[4-(3-Fluorophenyl-5-(hydroxymethyl)-1,3-thiazol-2-yl]-N-[4-(trifluoromethyl)phenyl]-1-piperidinecarboxamide TLC: Rf 0.31 (hexane:acetate=1:1);
$^1$H-NMR (CDCl$_3$): δ 7.58-7.37 (m, 7H), 7.12-7.04 (m, 1H), 6.54 (s, 1H), 4.91 (d, J=4.5 Hz, 2H), 4.25-4.13 (m, 2H), 3.32-3.20 (m, 1H), 3.20-3.05 (m, 2H), 2.30-2.18 (m, 2H), 2.08-2.00 (m, 1H), 1.97-1.82 (m, 2H).

Example 68 (4)

4-[4-(4-Fluorophenyl)-5-(hydroxymethyl)-1,3-thiazol-2-yl]-N-[4-(trifluoromethyl)phenyl]-1-piperidinecarboxamide TLC: Rf 0.31 (hexane:acetate=1:1);
$^1$H-NMR (CDCl$_3$): δ 7.68-7.61 (m, 2H), 7.58-7.44 (m, 4H), 7.18-7.09 (m, 2H), 6.53 (s, 1H), 4.88 (d, J=5.1 Hz, 2H), 4.25-4.13 (m, 2H), 3.32-3.20 (m, 1H), 3.20-3.05 (m, 2H), 2.30-2.18 (m, 2H), 2.02-1.82 (m, 3H).

Example 68 (5)

4-[5-(Hydroxymethyl)-4-(4-phenoxyphenyl)-1,3-thiazol-2-yl]-N-[4-(trifluoromethyl)phenyl]-1-piperidinecarboxamide TLC: Rf 0.29 (hexane:ethyl acetate, 1:1);
$^1$H-NMR (CDCl$_3$): δ 7.63 (d, J=9.0 Hz, 2H), 7.54 (d, J=9.0 Hz, 2H), 7.48 (d, J=9.0 Hz, 2H), 7.40-7.30 (m, 2H), 7.29-7.00 (m, 5H), 6.53 (s, 1H), 4.91 (d, J=6.0 Hz, 2H), 4.25-4.10 (m, 2H), 3.35-3.20 (m, 1H), 3.20-3.05 (m, 2H), 2.30-2.20 (m, 2H), 2.00-1.65 (m, 3H).

Example 68 (6)

4-[5-(Hydroxymethyl)-4-(2-methyl-2-propanil)-1,3-thiazol-2-yl]-N-[4-(trifluoromethyl)phenyl]-1-piperidinecarboxamide TLC: Rf 0.67 (hexane:acetate=1:1);
$^1$H-NMR (CDCl$_3$): δ 8.90 (s, 1H), 7.66 (d, J=8.4 Hz, 2H), 7.55 (d, J=8.4 Hz, 2H), 5.63 (t, J=5.1 Hz, 1H), 4.71 (d, J=5.1 Hz, 2H), 4.22-4.08 (m, 2H), 3.19-3.04 (m, 1H), 3.04-2.88 (m, 2H), 2.07-1.93 (m, 2H), 1.66-1.45 (m, 2H), 1.29 (s, 9H).

Example 68 (7)

4-[5-(2-Hydroxyethyl-4-phenyl-1,3-thiazol-2-yl]-N-[4-(trifluoromethyl)phenyl]-1-piperidinecarboxamide TLC: Rf 0.35 (hexane:acetate=1:2);
$^1$H-NMR (DMSO-d$_6$): δ 8.93 (s, 1H), 7.68 (d, J=8.4 Hz, 2H), 7.61 (d, J=7.5 Hz, 2H), 7.57 (d, J=8.4 Hz, 2H), 7.44 (t, J=7.5 Hz, 2H), 7.40-7.30 (m, 1H), 4.96 (t, J=5.3 Hz, 1H), 4.28-4.11 (m, 2H), 3.64 (q, J=5.3 Hz, 2H), 3.24 (tt, J=11.4, 3.6 Hz, 1H), 3.10-2.90 (m, 4H), 2.15-2.00 (m, 2H), 1.75-1.54 (m, 2H).

Reference Example Compound:
4-(4-Phenyl-1,3-thiazol-2-yl)-N-(3-pyridyl)-1-piperidinecarboxamide

[Chemical Formula 53]

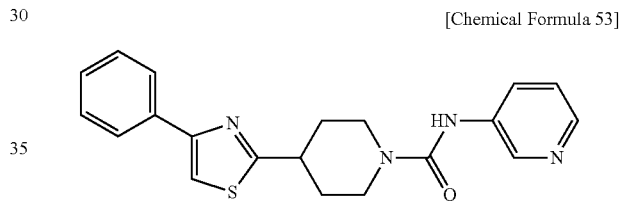

In place of 2-bromo-1-phenylpropan-1-one of Example 33, 2-bromo-1-phenylethan-1-one was subjected to the operations according to Example 33→Example 34→Example 36 to give the title compound having the following physical properties.

TLC: Rf 0.50 (methanol:acetate=1:19);
$^1$H-NMR (DMSO-d6): δ 8.72 (s, 1H), 8.63-8.62 (m, 1H), 8.11 (dd, J=1.5, 4.8 Hz, 1H), 7.98 (s, 1H), 7.95-7.84 (m, 3H), 7.45-7.35 (m, 2H), 7.35-7.20 (m, 2H), 4.25-4.15 (m, 2H), 3.40-3.30 (m, 1H), 3.10-2.95 (m, 2H), 2.20-2.10 (m, 2H), 1.80-1.60 (m, 2H).

Pharmacological Example 1

IP1 (Inositol Monophosphate) Assay

An ALXR/Gα16 expression CHO-K1 cell strain having $3 \times 10^4$ cells/100 μL was seeded on a 96-well plate using an F-12 culture medium (10% FBS, 100 μmol/L nonessential amino acid, 100 U/mL penicillin, 100 μg/mL streptomycin, 0.25 μg/mL Amphotericin B, 400 μg/mL Geneticin, and 5 μg/mL Puromycin), and cultured at 37° C. in 5% CO$_2$ overnight. After the culture supernatant was removed, a 70-μL Basal buffer (10 mmol/L HEPES, 1 mmol/L CaCl$_2$, 0.5 mmol/L MgCl$_2$, 4.2 mmol/L KCl, 146 mmol/L NaCl, 5.5 mmol/L glucose, 50 mmol/L LiCl), each buffer containing one of the compounds and the reference example compound, was added. Here, as the medium group, a Basal buffer containing 1% DMSO was used. After the cell strain was further cultured at 37° C. in 5% $CO_2$ for 30 minutes, IP1-d2 conjugate (Cisbio) and Anti-IP1 cryptate Tb conjugate (Cisbio) diluted with Lysis buffer (Cisbio) were each added in an amount of 15 μL. The culture was allowed to stand for 1 hour under shaded conditions at room temperature. Subsequently, using EnVision (PerkinElmer), measurement was performed at an excitation wavelength of 320 nm and fluorescence wavelengths of 620 nm and 665 nm, and the fluorescence ratio 665 nm/620 nm was calculated. With respect to the IP1 concentration, a calibration curve was produced using an IP1 calibrator (Cisbio) to be converted into concentration. The measured values were analyzed using XLfit (IDBS). Table 1 shows IP1 concentrations (nmol/L) resulting from the addition of each compound at a concentration of 3 μM as well as the addition of media (medium group).

[Results]

The compound of the present invention enhanced the IP1 concentration as compared with the medium group. Meanwhile, in the case of the reference example compound, no enhancement was seen.

From the results, it was confirmed that the compound of the present invention have ALXR agonist activity.

TABLE 1

| Example Compound | IP1 Concentration (nmol/L) |
| --- | --- |
| 27(1) | 539.3 |
| 29(2) | 853.7 |
| 40 | 789.9 |
| 51 | 592.1 |
| 60 | 1020.9 |
| Reference Example Compound | 282.5 |
| Medium | 293.6 |

Preparation Example 1

The following components were mixed in the usual manner and then tableted, thereby giving 10,000 tablets containing 5 mg of active ingredient per tablet.
4-Hydroxy-4-(4-phenyl-1,3-thiazol-2-yl)-N-[4-(trifluoromethyl)phenyl]-1-piperidinecarboxamide: 50 g
Carboxy methylcellulose calcium (disintegrator): 20 g
Magnesium stearate (lubricant): 10 g
Microcrystalline cellulose: 920 g Preparation Example 2

The following components were mixed in the usual manner, and then the solution was sterilized in the usual manner. Ampules were each filled with 5 mL of the solution and lyophilized in the usual manner, thereby giving 10,000 ampules containing 20 mg of active ingredient per ampule.
4-Hydroxy-4-(4-phenyl-1,3-thiazol-2-yl)-N-[4-(trifluoromethyl)phenyl]-1-piperidinecarboxamide: 200 g
Mannitol: 20 g
Distilled water: 50 L

INDUSTRIAL APPLICABILITY

The compound of the present invention have ALXR agonist activity and thus are useful as effective agents for preventing and/or treating autoimmune diseases, chronic inflammatory diseases, asthma, pulmonary fibrosis, atopic dermatitis, ischemia-reperfusion injury, myocardial infarction, Alzheimer's disease, etc.

What is claimed is:

1. A compound of the following formula (I), or a salt thereof:

(I)

wherein
A is a bond, —C(=O)—, —(C($R^5$)$_2$)$_m$—, —CH=CH—, or —C(=O)NH— (wherein $R^5$ is a hydrogen atom, a hydroxyl group, a methoxy group, or an ethoxy group, and m is an integer of 1 or 2),
ring L is a phenyl group,
$R^1$ is a pyridyl group optionally substituted with one to three Ys wherein Y is a hydroxyl group, a halogen atom, a cyano group, a $C_{1-4}$ alkyl group, a $C_{1-4}$ alkoxy group, or a phenoxy group,
$R^2$ is a hydrogen atom, a $C_{1-3}$ alkyl group, a cyano group, —(C($R^6$)$_2$)$_p$OH wherein $R^6$ is a hydrogen atom or a methyl group, and p is an integer of 1 or 2, or —(CH$_2$)$_q$COR$^7$ wherein $R^7$ is a hydroxyl group, a methyl group, an amino group, a methoxy group, or an ethoxy group, and q represents an integer of 0 or 1,
$R^3$ is a hydrogen atom, a hydroxyl group, a halogen atom, a $C_{1-4}$ alkyl group, a cyano group, or —NHR$^8$ wherein $R^8$ is a hydrogen atom, an acetyl group, or a methylsulfonyl group, and
$R^4$ is a hydroxyl group, a halogen atom, a $C_{1-4}$ alkyl group, or an amino group, and
n is an integer of 0 to 3,
with the proviso that a plurality of Ys, $R^4$s, $R^5$s, and $R^6$s may be the same or different, respectively.

2. The compound according to claim 1, wherein A is a bond, or a salt thereof.

3. The compound according to claim 1, wherein $R^3$ is a hydrogen atom or a hydroxyl group, or a salt thereof.

4. The compound according to claim 1, wherein $R^2$ is a hydrogen atom, a methyl group, or —CH$_2$OH, or a salt thereof.

5. The compound according to claim 1, wherein $R^1$ is a pyridyl group optionally substituted with one Y, or a salt thereof.

6. The compound according to claim 1, wherein n is 0, or a salt thereof.

7. The compound according to claim 1, wherein the compound of the formula (I) is represented by the following formula (I-1):

(I-1)

wherein $R^{1-1}$ is a pyridyl group optionally substituted with one Y, ring $L^1$ is a phenyl group wherein the ring $L^1$ is not substituted except for trifluoromethyl group and —NH— group attached thereto, $R^{2-1}$ is a hydrogen atom or a methyl group, $R^{3-1}$ is a hydrogen atom or a hydroxyl group, and other symbols are as defined in claim 1, or a salt thereof.

8. The compound according to claim 7, wherein in the formula (I-1), the formula

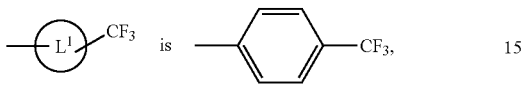

or a salt thereof.

9. The compound according to claim 8, wherein the compound of the formula (I-1) is 4-[4-(3-pyridyl)-1,3-thiazol-2-yl]-N-[4-(trifluoromethyl)phenyl]-1-piperidinecarboxamide, or a salt thereof.

10. A pharmaceutical composition comprising a compound represented by general formula (I) as defined in claim 1, or a salt thereof as an active ingredient, and an inert carrier.

* * * * *